(12) United States Patent
Ritland

(10) Patent No.: US 7,763,047 B2
(45) Date of Patent: Jul. 27, 2010

(54) PEDICLE SCREW CONNECTOR APPARATUS AND METHOD

(76) Inventor: Stephen Ritland, 1150 N. San Francisco St., Flagstaff, AZ (US) 86001

( * ) Notice: Subject to any disclaimer, the term of this patent is extended or adjusted under 35 U.S.C. 154(b) by 0 days.

(21) Appl. No.: 10/371,317

(22) Filed: Feb. 20, 2003

(65) Prior Publication Data
US 2003/0171751 A1  Sep. 11, 2003

Related U.S. Application Data

(60) Provisional application No. 60/359,246, filed on Feb. 20, 2002.

(51) Int. Cl.
*A61B 17/70* (2006.01)
(52) U.S. Cl. ........................ 606/246; 606/278
(58) Field of Classification Search .................. 606/61, 606/72–73, 69, 70; 403/289, 290, 338, 341, 403/398; 411/81, 87, 95, 136, 147, 151
See application file for complete search history.

(56) References Cited

U.S. PATENT DOCUMENTS

| 2,191 | A | 7/1841 | Pitney |
|---|---|---|---|
| 569,839 | A | 10/1896 | Roeloffs |
| 605,652 | A | 6/1898 | Pitt |
| 1,090,746 | A | 3/1914 | Nourse |
| 1,097,978 | A | 5/1914 | Johnson |
| 3,467,079 | A | 9/1969 | James |
| 3,470,872 | A | 10/1969 | Grieshaber |
| 3,875,595 | A | 4/1975 | Froning |
| 3,893,454 | A | 7/1975 | Hagelin |
| 4,041,939 | A | 8/1977 | Hall |
| 4,232,660 | A | 11/1980 | Coles |
| 4,440,168 | A | 4/1984 | Warren |

(Continued)

FOREIGN PATENT DOCUMENTS

CA  2320821  8/1999

(Continued)

OTHER PUBLICATIONS

Notification of Transmittal of the International Search Report or Declaration (PCT Rule 44.1) for PCT Application Serial No. PCT/US03/05086 filed Feb. 20, 2003.

(Continued)

*Primary Examiner*—Eduardo C Robert
*Assistant Examiner*—David Comstock
(74) *Attorney, Agent, or Firm*—Holme Roberts & Owen LLP

(57) ABSTRACT

A low-profile rod connector is disclosed that includes two substantially conical surfaces that allows two rods to be secured together. The device is easily manipulated and occupies very little space. The connector allows for the rods to be oriented at a number of different positions prior to securing the rods in a final orientation. Medical implants utilizing the present invention include surgical implants for spine stabilization. One particular application comprises securing the shaft of a pedicle screw to a spinal rod. In such application, since the connector is relatively small, displacement and disruption to nearby tissue is minimized. The connector also has application to external fixation systems which are conducted exterior of the skin surface, as well as other mechanical devices.

37 Claims, 8 Drawing Sheets

U.S. PATENT DOCUMENTS

| | | | |
|---|---|---|---|
| 4,481,947 A | 11/1984 | Chester | |
| 4,545,374 A | 10/1985 | Jacobson | |
| 4,573,448 A | 3/1986 | Kambin | |
| 4,617,922 A | 10/1986 | Griggs | |
| 4,620,460 A | 11/1986 | Gonzales, Jr. | |
| 4,686,972 A | 8/1987 | Kurland | |
| 4,736,738 A | 4/1988 | Lipovsek | |
| 4,743,260 A | 5/1988 | Burton | |
| 4,747,394 A | 5/1988 | Watanabe | |
| 4,798,111 A | 1/1989 | Cheeseman | |
| 4,803,976 A | 2/1989 | Frigg | |
| 4,817,587 A | 4/1989 | Janese | |
| 4,862,891 A | 9/1989 | Smith | |
| 4,863,423 A | 9/1989 | Wallace | |
| 4,882,958 A | 11/1989 | McNeeley | |
| 4,889,112 A | 12/1989 | Schachner et al. | |
| 4,995,875 A | 2/1991 | Coes | |
| 5,002,542 A | 3/1991 | Frigg | |
| 5,002,576 A | 3/1991 | Fuhrmann et al. | |
| 5,018,507 A | 5/1991 | Montaldi | |
| 5,024,213 A | 6/1991 | Asher et al. | |
| 5,026,373 A | 6/1991 | Ray et al. | |
| 5,030,220 A | 7/1991 | Howland | |
| 5,030,223 A | 7/1991 | Anderson et al. | |
| 5,035,232 A | 7/1991 | Lutze et al. | |
| 5,048,379 A | 9/1991 | Gramera | |
| 5,052,373 A | 10/1991 | Michelson | |
| 5,055,104 A | 10/1991 | Ray | |
| 5,084,043 A | 1/1992 | Hertzmann | |
| 5,098,435 A | 3/1992 | Stednitz | |
| 5,106,376 A | 4/1992 | Mononen | |
| 5,129,900 A | 7/1992 | Asher et al. | |
| 5,133,720 A | 7/1992 | Greenberg | |
| 5,135,525 A | 8/1992 | Biscoping | |
| 5,148,724 A | 9/1992 | Rexford | |
| 5,158,543 A | 10/1992 | Lazarus | |
| 5,165,306 A | 11/1992 | Hellon | |
| 5,195,541 A | 3/1993 | Obenchain | |
| 5,217,007 A | 6/1993 | Ciaglia | |
| 5,275,600 A | 1/1994 | Allard et al. | |
| 5,275,611 A | 1/1994 | Behl | |
| 5,279,567 A | 1/1994 | Ciaglia | |
| 5,292,309 A | 3/1994 | Van Tassel | |
| 5,303,694 A | 4/1994 | Mikhail | |
| 5,306,275 A * | 4/1994 | Bryan | 606/61 |
| 5,306,309 A | 4/1994 | Wagner et al. | |
| 5,312,360 A | 5/1994 | Behl | |
| 5,312,405 A | 5/1994 | Korotko et al. | |
| 5,330,473 A * | 7/1994 | Howland | 606/250 |
| 5,330,474 A | 7/1994 | Lin | |
| 5,330,476 A | 7/1994 | Hiot et al. | |
| 5,356,413 A | 10/1994 | Martins et al. | |
| 5,363,841 A | 11/1994 | Coker | |
| 5,415,661 A | 5/1995 | Holmes | |
| 5,431,639 A | 7/1995 | Shaw | |
| 5,431,651 A | 7/1995 | Goble | |
| D361,381 S | 8/1995 | Koros et al. | |
| 5,439,464 A | 8/1995 | Shapiro | |
| 5,466,238 A | 11/1995 | Lin | |
| 5,472,426 A | 12/1995 | Bonati | |
| 5,474,555 A | 12/1995 | Puno et al. | |
| 5,480,401 A | 1/1996 | Navas | |
| 5,484,440 A | 1/1996 | Allard | |
| 5,489,274 A | 2/1996 | Chu | |
| 5,489,308 A | 2/1996 | Kuslich et al. | |
| 5,498,262 A * | 3/1996 | Bryan | 606/61 |
| 5,499,983 A * | 3/1996 | Hughes | 606/61 |
| 5,501,684 A * | 3/1996 | Schlapfer et al. | 606/73 |
| 5,512,038 A | 4/1996 | O'Neal et al. | |
| 5,545,166 A | 8/1996 | Howland | |
| 5,558,622 A | 9/1996 | Greenberg | |
| 5,562,663 A | 10/1996 | Wisnewski et al. | |
| 5,565,502 A | 10/1996 | Glimcher et al. | |
| 5,569,300 A | 10/1996 | Redmon | |
| 5,584,831 A | 12/1996 | McKay | |
| 5,584,833 A * | 12/1996 | Fournet-Fayard et al. | 606/61 |
| 5,591,166 A | 1/1997 | Bernhardt et al. | |
| 5,591,235 A | 1/1997 | Kuslich | |
| 5,593,409 A | 1/1997 | Michelson | |
| 5,601,550 A | 2/1997 | Esser | |
| 5,603,714 A | 2/1997 | Kaneda et al. | |
| 5,611,778 A | 3/1997 | Brinon | |
| 5,613,968 A | 3/1997 | Lin | |
| 5,628,740 A | 5/1997 | Mullane | |
| 5,643,263 A * | 7/1997 | Simonson | 606/61 |
| 5,643,264 A | 7/1997 | Sherman et al. | |
| 5,645,544 A | 7/1997 | Tai et al. | |
| 5,645,599 A | 7/1997 | Samani | |
| 5,667,506 A | 9/1997 | Sutterlin | |
| 5,683,392 A | 11/1997 | Richelsoph et al. | |
| 5,683,463 A | 11/1997 | Godefroy et al. | |
| 5,687,739 A | 11/1997 | McPherson | |
| 5,690,632 A | 11/1997 | Schwartz et al. | |
| 5,691,397 A | 11/1997 | Glimcher et al. | |
| 5,695,993 A | 12/1997 | Fukudome et al. | |
| 5,702,455 A | 12/1997 | Saggar | |
| 5,716,355 A * | 2/1998 | Jackson et al. | 606/61 |
| 5,716,415 A | 2/1998 | Steffee | |
| 5,725,528 A | 3/1998 | Errico et al. | |
| 5,735,850 A | 4/1998 | Baumgartner et al. | |
| 5,735,851 A | 4/1998 | Errico et al. | |
| 5,735,899 A | 4/1998 | Schwartz et al. | |
| 5,743,853 A | 4/1998 | Lauderdale | |
| 5,746,720 A | 5/1998 | Stouder, Jr. | |
| 5,746,741 A | 5/1998 | Kraus et al. | |
| 5,752,957 A | 5/1998 | Ralph et al. | |
| 5,766,221 A | 6/1998 | Benderev et al. | |
| 5,766,253 A | 6/1998 | Brosnahan, III | |
| 5,772,582 A | 6/1998 | Huttner et al. | |
| 5,782,832 A | 7/1998 | Larsen et al. | |
| 5,785,648 A | 7/1998 | Min | |
| 5,785,710 A | 7/1998 | Michelson | |
| 5,785,712 A | 7/1998 | Runciman et al. | |
| 5,792,044 A | 8/1998 | Foley | |
| 5,797,912 A | 8/1998 | Runciman et al. | |
| 5,800,435 A | 9/1998 | Errico et al. | |
| 5,810,816 A * | 9/1998 | Roussouly et al. | 606/61 |
| 5,810,817 A * | 9/1998 | Roussouly et al. | 606/61 |
| D399,955 S | 10/1998 | Koros et al. | |
| 5,816,257 A | 10/1998 | Chin | |
| 5,827,328 A | 10/1998 | Buttermann | |
| 5,836,948 A | 11/1998 | Zucherman et al. | |
| RE36,020 E | 12/1998 | Moore et al. | |
| 5,851,207 A | 12/1998 | Cesarone | |
| 5,860,977 A | 1/1999 | Zucherman et al. | |
| 5,865,847 A | 2/1999 | Kohrs et al. | |
| 5,865,848 A | 2/1999 | Baker | |
| 5,876,404 A | 3/1999 | Zucherman et al. | |
| 5,882,344 A | 3/1999 | Stouder, Jr. | |
| 5,885,285 A | 3/1999 | Simonson | |
| 5,885,299 A | 3/1999 | Winslow et al. | |
| 5,885,300 A | 3/1999 | Tokuhashi et al. | |
| 5,891,147 A | 4/1999 | Moskovitz et al. | |
| 5,895,352 A | 4/1999 | Kleiner | |
| 5,895,390 A | 4/1999 | Moran et al. | |
| 5,897,593 A | 4/1999 | Kohrs et al. | |
| 5,899,901 A | 5/1999 | Middleton | |
| 5,902,231 A | 5/1999 | Foley | |
| 5,902,304 A * | 5/1999 | Walker et al. | 606/71 |
| 5,904,650 A | 5/1999 | Wells | |
| 5,906,616 A | 5/1999 | Pavlov et al. | |
| 5,913,818 A | 6/1999 | Co et al. | |
| 5,928,139 A | 7/1999 | Koros | |
| 5,928,233 A | 7/1999 | Apfelbaum et al. | |

| Patent No. | Date | Inventor |
|---|---|---|
| 5,931,838 A | 8/1999 | Vito |
| 5,938,663 A * | 8/1999 | Petreto ............ 606/61 |
| 5,944,658 A | 8/1999 | Koros et al. |
| 5,947,965 A * | 9/1999 | Bryan ............ 606/61 |
| 5,954,635 A | 9/1999 | Foley |
| 5,954,671 A | 9/1999 | O'Neil |
| 5,961,516 A | 10/1999 | Graf |
| 5,967,970 A | 10/1999 | Cowan |
| 5,968,098 A | 10/1999 | Winslow |
| 5,971,920 A | 10/1999 | Nagel |
| 5,976,135 A * | 11/1999 | Sherman et al. ............ 606/61 |
| 5,976,146 A | 11/1999 | Ogawa |
| 5,984,924 A | 11/1999 | Asher et al. |
| 5,996,447 A | 12/1999 | Bayouth |
| 5,997,539 A | 12/1999 | Errico et al. |
| 6,004,322 A * | 12/1999 | Bernstein ............ 606/61 |
| 6,007,487 A | 12/1999 | Foley et al. |
| 6,010,520 A | 1/2000 | Pattison |
| 6,017,342 A | 1/2000 | Rinner |
| 6,027,533 A * | 2/2000 | Olerud ............ 623/16.11 |
| 6,045,579 A | 4/2000 | Hochshuler et al. |
| 6,048,342 A | 4/2000 | Zucherman et al. |
| 6,050,997 A * | 4/2000 | Mullane ............ 606/61 |
| 6,063,088 A | 5/2000 | Winslow |
| 6,068,630 A | 5/2000 | Zucherman et al. |
| 6,074,390 A | 6/2000 | Zucherman et al. |
| 6,074,393 A | 6/2000 | Sitoto |
| 6,080,155 A | 6/2000 | Michelson |
| 6,080,193 A | 6/2000 | Hochshuler et al. |
| 6,081,741 A | 6/2000 | Hollis |
| 6,083,225 A | 7/2000 | Winslow et al. |
| 6,083,226 A | 7/2000 | Fiz |
| 6,090,112 A | 7/2000 | Zucherman et al. |
| 6,102,948 A | 8/2000 | Brosnahan, III |
| 6,113,602 A | 9/2000 | Sand |
| 6,117,137 A | 9/2000 | Halm et al. |
| 6,117,174 A | 9/2000 | Nolan |
| 6,120,434 A | 9/2000 | Kimura |
| 6,120,506 A | 9/2000 | Kohrs et al. |
| 6,123,705 A | 9/2000 | Michelson |
| 6,123,706 A * | 9/2000 | Lange ............ 606/61 |
| 6,132,430 A | 10/2000 | Wagner |
| D433,296 S | 11/2000 | Yamakawa |
| 6,146,383 A * | 11/2000 | Studer et al. ............ 606/61 |
| 6,149,652 A | 11/2000 | Zucherman et al. |
| 6,149,686 A | 11/2000 | Kuslich et al. |
| 6,152,871 A | 11/2000 | Foley |
| 6,152,926 A | 11/2000 | Zucherman et al. |
| 6,156,006 A | 12/2000 | Brosens |
| 6,156,038 A | 12/2000 | Zucherman et al. |
| 6,159,179 A | 12/2000 | Simonson |
| 6,162,170 A | 12/2000 | Foley |
| 6,162,236 A | 12/2000 | Osada |
| D436,513 S | 1/2001 | Yamakawa |
| 6,176,823 B1 | 1/2001 | Foley |
| 6,176,861 B1 * | 1/2001 | Bernstein et al. ............ 606/61 |
| 6,179,838 B1 * | 1/2001 | Fiz ............ 606/61 |
| D438,074 S | 2/2001 | Marr |
| 6,183,471 B1 | 2/2001 | Zucherman et al. |
| 6,187,005 B1 * | 2/2001 | Brace et al. ............ 606/61 |
| 6,190,387 B1 | 2/2001 | Zucherman et al. |
| 6,190,414 B1 | 2/2001 | Young et al. |
| 6,196,696 B1 | 3/2001 | Shiao |
| 6,196,969 B1 | 3/2001 | Bester et al. |
| 6,197,002 B1 | 3/2001 | Peterson |
| 6,206,822 B1 | 3/2001 | Foley |
| 6,206,826 B1 | 3/2001 | Mathews et al. |
| 6,206,885 B1 | 3/2001 | Ghahremani et al. |
| 6,206,922 B1 | 3/2001 | Zdeblick et al. |
| 6,206,923 B1 | 3/2001 | Boyd et al. |
| 6,210,413 B1 * | 4/2001 | Justis et al. ............ 606/61 |
| 6,214,004 B1 | 4/2001 | Coker |
| 6,217,509 B1 | 4/2001 | Foley |
| 6,224,597 B1 | 5/2001 | Coker |
| 6,224,608 B1 | 5/2001 | Ciccolella |
| 6,224,631 B1 | 5/2001 | Kohrs |
| 6,231,575 B1 * | 5/2001 | Krag ............ 606/61 |
| 6,235,030 B1 | 5/2001 | Zucherman et al. |
| 6,238,397 B1 | 5/2001 | Zucherman et al. |
| 6,245,072 B1 | 6/2001 | Zdeblick et al. |
| 6,248,104 B1 * | 6/2001 | Chopin et al. ............ 606/61 |
| 6,248,106 B1 | 6/2001 | Ferree |
| 6,258,097 B1 | 7/2001 | Cook |
| 6,261,287 B1 | 7/2001 | Metz-Stavenhagen |
| 6,264,658 B1 | 7/2001 | Lee et al. |
| 6,267,763 B1 | 7/2001 | Castro |
| 6,267,764 B1 | 7/2001 | Elberg |
| 6,267,765 B1 * | 7/2001 | Taylor et al. ............ 606/61 |
| 6,270,498 B1 | 8/2001 | Michelson |
| 6,273,914 B1 * | 8/2001 | Papas ............ 623/17.11 |
| 6,283,966 B1 | 9/2001 | Houfburg |
| 6,287,309 B1 * | 9/2001 | Baccelli et al. ............ 606/61 |
| 6,287,313 B1 | 9/2001 | Sasso |
| 6,287,343 B1 | 9/2001 | Kuslich et al. |
| 6,290,700 B1 | 9/2001 | Schmotzer |
| 6,293,949 B1 | 9/2001 | Justis et al. |
| 6,296,609 B1 | 10/2001 | Brau |
| 6,299,614 B1 * | 10/2001 | Kretschmer et al. ............ 606/61 |
| 6,302,842 B1 | 10/2001 | Auerbach et al. |
| 6,309,390 B1 * | 10/2001 | Le Couedic et al. ............ 606/61 |
| 6,309,391 B1 * | 10/2001 | Crandall et al. ............ 606/61 |
| 6,312,432 B1 | 11/2001 | Leppelmeier |
| 6,332,883 B1 | 12/2001 | Zucherman et al. |
| 6,342,057 B1 | 1/2002 | Brace |
| 6,348,058 B1 | 2/2002 | Melkent et al. |
| 6,354,176 B1 | 3/2002 | Nordlin |
| 6,355,038 B1 * | 3/2002 | Pisharodi ............ 606/61 |
| 6,361,541 B1 | 3/2002 | Barnhart |
| 6,368,320 B1 | 4/2002 | Le Couedic et al. |
| 6,368,350 B1 | 4/2002 | Erickson et al. |
| 6,368,351 B1 | 4/2002 | Glenn et al. |
| 6,371,959 B1 | 4/2002 | Trice |
| 6,371,968 B1 | 4/2002 | Kogasaka |
| 6,391,058 B1 | 5/2002 | Kuslich et al. |
| 6,395,033 B1 | 5/2002 | Pepper |
| 6,418,821 B1 | 7/2002 | Yamakawa |
| 6,425,901 B1 | 7/2002 | Zhu et al. |
| 6,428,472 B1 | 8/2002 | Haas |
| 6,440,169 B1 | 8/2002 | Elberg et al. |
| 6,440,170 B1 | 8/2002 | Jackson |
| 6,443,953 B1 | 9/2002 | Perra et al. |
| 6,443,989 B1 | 9/2002 | Jackson |
| 6,461,330 B1 | 10/2002 | Miyagi |
| 6,461,359 B1 | 10/2002 | Tribus et al. |
| 6,471,724 B2 | 10/2002 | Zdeblick et al. |
| 6,475,219 B1 | 11/2002 | Shelokov |
| 6,478,798 B1 * | 11/2002 | Howland ............ 606/61 |
| D466,766 S | 12/2002 | Marty |
| 6,506,151 B2 | 1/2003 | Estes et al. |
| 6,520,907 B1 | 2/2003 | Foley |
| 6,524,238 B2 | 2/2003 | Velikaris et al. |
| 6,530,880 B2 | 3/2003 | Pagliuca |
| 6,530,926 B1 | 3/2003 | Davison |
| 6,540,756 B1 | 4/2003 | Vaughan |
| 6,551,320 B2 | 4/2003 | Lieberman |
| 6,554,831 B1 | 4/2003 | Rivard et al. |
| 6,562,046 B2 | 5/2003 | Sasso |
| 6,562,073 B2 | 5/2003 | Foley |
| 6,565,569 B1 * | 5/2003 | Assaker et al. ............ 606/61 |
| 6,569,164 B1 * | 5/2003 | Assaker et al. ............ 606/61 |
| 6,576,017 B2 | 6/2003 | Foley |
| 6,579,292 B2 * | 6/2003 | Taylor ............ 606/61 |
| 6,585,738 B1 * | 7/2003 | Mangione et al. ............ 606/61 |
| 6,585,769 B1 | 7/2003 | Muhanna et al. |
| 6,595,993 B2 | 7/2003 | Donno et al. |
| 6,610,062 B2 * | 8/2003 | Bailey et al. ............ 606/61 |

| | | |
|---|---|---|
| 6,626,904 B1 | 9/2003 | Jammet et al. |
| 6,626,906 B1 * | 9/2003 | Young .................. 606/61 |
| 6,648,887 B2 * | 11/2003 | Ashman ................. 606/61 |
| 6,671,725 B1 | 12/2003 | Noel, Jr. et al. |
| 6,676,661 B1 * | 1/2004 | Martin Benlloch et al. .... 606/61 |
| 6,679,833 B2 | 1/2004 | Smith et al. |
| 6,682,532 B2 | 1/2004 | Johnson et al. |
| 6,685,705 B1 * | 2/2004 | Taylor ................. 606/61 |
| 6,692,434 B2 | 2/2004 | Ritland |
| 6,736,816 B2 | 5/2004 | Ritland |
| 6,743,257 B2 | 6/2004 | Castro |
| 6,749,613 B1 | 6/2004 | Conchy et al. |
| 6,749,614 B2 | 6/2004 | Teitelbaum |
| 6,752,832 B2 | 6/2004 | Neumann |
| 6,761,719 B2 | 7/2004 | Justis et al. |
| 6,783,528 B2 * | 8/2004 | Vincent-Prestigiacomo .. 606/61 |
| 6,851,430 B2 | 2/2005 | Tsou |
| 6,874,480 B1 | 4/2005 | Ismailov |
| 6,875,211 B2 | 4/2005 | Nichols et al. |
| 6,916,319 B2 * | 7/2005 | Munting ................. 606/61 |
| 6,916,330 B2 | 7/2005 | Simonson |
| 6,929,606 B2 | 8/2005 | Ritland |
| 6,951,538 B2 | 10/2005 | Ritland |
| 6,955,678 B2 | 10/2005 | Gabriel et al. |
| 6,966,910 B2 | 11/2005 | Ritland |
| 6,974,480 B2 | 12/2005 | Messerli et al. |
| 6,991,632 B2 | 1/2006 | Ritland |
| 7,008,431 B2 | 3/2006 | Simonson |
| 7,166,073 B2 | 1/2007 | Ritland |
| 7,207,992 B2 | 4/2007 | Ritland |
| 2001/0005796 A1 | 6/2001 | Zdeblick et al. |
| 2001/0010021 A1 | 7/2001 | Boyd et al. |
| 2001/0012942 A1 | 8/2001 | Estes |
| 2001/0027320 A1 | 10/2001 | Sasso |
| 2001/0047207 A1 | 11/2001 | Michelson |
| 2002/0011135 A1 | 1/2002 | Hall |
| 2002/0016592 A1 | 2/2002 | Branch |
| 2002/0022764 A1 | 2/2002 | Smith |
| 2002/0029082 A1 | 3/2002 | Muhanna |
| 2002/0049368 A1 | 4/2002 | Ritland |
| 2002/0052603 A1 | 5/2002 | Nichols et al. |
| 2002/0058948 A1 | 5/2002 | Arlettaz |
| 2002/0068973 A1 | 6/2002 | Jackson |
| 2002/0068975 A1 | 6/2002 | Teitelbaum et al. |
| 2002/0077632 A1 | 6/2002 | Tsou |
| 2002/0082695 A1 | 6/2002 | Neumann |
| 2002/0107571 A1 | 8/2002 | Foley |
| 2002/0107572 A1 | 8/2002 | Foley et al. |
| 2002/0111625 A1 | 8/2002 | Richelsoph et al. |
| 2002/0120270 A1 | 8/2002 | Trieu et al. |
| 2002/0123668 A1 | 9/2002 | Ritland |
| 2002/0143235 A1 | 10/2002 | Pagliuca |
| 2003/0045874 A1 | 3/2003 | Thomas |
| 2003/0083688 A1 | 5/2003 | Simonson |
| 2003/0083689 A1 | 5/2003 | Simonson |
| 2003/0093078 A1 | 5/2003 | Ritland |
| 2003/0109880 A1 | 6/2003 | Shirado et al. |
| 2003/0139812 A1 | 7/2003 | Garcia et al. |
| 2003/0144665 A1 | 7/2003 | Munting |
| 2003/0171749 A1 | 9/2003 | Le Couedic et al. |
| 2003/0171751 A1 | 9/2003 | Ritland |
| 2003/0187431 A1 | 10/2003 | Simonson |
| 2003/0191470 A1 | 10/2003 | Ritland |
| 2003/0195087 A1 | 10/2003 | Moore et al. |
| 2003/0220689 A1 | 11/2003 | Ritland |
| 2003/0236447 A1 | 12/2003 | Ritland |
| 2004/0002708 A1 | 1/2004 | Ritland |
| 2004/0106997 A1 | 6/2004 | Lieberson |
| 2004/0138534 A1 | 7/2004 | Ritland |
| 2004/0172023 A1 | 9/2004 | Ritland |
| 2004/0181223 A1 | 9/2004 | Ritland |
| 2004/0254428 A1 | 12/2004 | Ritland |
| 2005/0004593 A1 | 1/2005 | Simonson |
| 2005/0020920 A1 | 1/2005 | Ritland |
| 2005/0027360 A1 | 2/2005 | Webb et al. |
| 2005/0143737 A1 | 6/2005 | Paffard et al. |
| 2005/0149191 A1 | 7/2005 | Cragg et al. |
| 2005/0203517 A1 | 9/2005 | Jahng et al. |
| 2005/0203519 A1 | 9/2005 | Harms et al. |
| 2005/0209694 A1 | 9/2005 | Loeb |
| 2005/0228233 A1 | 10/2005 | Ritland |
| 2006/0009768 A1 | 1/2006 | Ritland |
| 2006/0041259 A1 | 2/2006 | Paul et al. |
| 2006/0064090 A1 | 3/2006 | Park |
| 2006/0069390 A1 | 3/2006 | Frigg et al. |
| 2006/0079899 A1 | 4/2006 | Ritland |
| 2006/0195087 A1 | 8/2006 | Moore et al. |
| 2007/0016193 A1 | 1/2007 | Ritland |

FOREIGN PATENT DOCUMENTS

| | | |
|---|---|---|
| EP | 0 820 731 A3 | 1/1998 |
| EP | 1585427 | 10/2005 |
| EP | 1658815 | 10/2005 |
| FR | 2735351 | 12/1996 |
| FR | 2796828 | 2/2001 |
| FR | 2799949 | 4/2001 |
| FR | 2812185 | 2/2002 |
| JP | 2000-33091 | 2/2000 |
| WO | 95/08298 | 3/1995 |
| WO | 97/06742 | 2/1997 |
| WO | 97/32533 | 12/1997 |
| WO | WO 99/40866 | 8/1999 |
| WO | WO 00/18306 | 4/2000 |
| WO | 00/57801 | 10/2000 |
| WO | 01/64144 | 9/2001 |
| WO | 01/67973 | 9/2001 |
| WO | WO 02/02022 | 1/2002 |
| WO | WO 02/07621 | 1/2002 |
| WO | 02/36026 | 5/2002 |
| WO | 02/060330 | 8/2002 |
| WO | WO 02/060330 | 8/2002 |
| WO | 02/102259 | 12/2002 |
| WO | WO 03/026523 | 4/2003 |
| WO | WO 03/073908 | 9/2003 |
| WO | WO 03/094699 | 11/2003 |
| WO | WO 2004/075778 | 9/2004 |
| WO | WO 2004/089244 | 10/2004 |

OTHER PUBLICATIONS

U.S. Appl. No. 10/788,172, filed Feb. 25, 2004, Ritland.
U.S. Appl. No. 10/776,094, filed Feb. 10, 2004, Ritland.
U.S. Appl. No. 11/069,390, Ritland.
Caspar; "Technique of Microsurgery: Microsurgery of the Lumbar Spine: Principles and Techniques in Spine Surgery"; *Aspen Publications*; 1990; 105-122.
Hilton et al.; "Meditronic Sofamor Danek METRX Microdiscectomy Surgical Technique Brochure"; 2000.
Kambin; "Arthroscopic Microdiscectomy: Minimal Intervention in Spinal Surgery"; *National Library of Medicine*; 1991; 67-100.
Kambin; "Percutaneous Posterolateral Discectomy"; *Clinclal Orthopaedics and Related Research, Section II*; 145-154119.
Savitz; "Same-Day Microsurgical Arthroscopic Latera-Approach Laser-Assisted (SMALL) Fluoroscopic Discectomy"; *Journal of Neurosurgery*; Jun. 1994; 1039-1045.
Schaffer et al.; "Percutaneous Posterolateral Lumbar Discectomy and Decompression with a 6.9 Millimeter Cannula"; *Journal of Bone and Joint Surgery*; 1991; 822-831.
Sofamor Danek Video Systems Brochure.
Wiltse; "New Uses and Refinements of the Paraspinal Approach to the Lumbar Spine"; *Spine*; 1988; 13(6):696-706.
U.S. Appl. No. 10/165,991, Simonson.
U.S. Appl. No. 11/425,987, Ritland.
China Chemical Reporter, "Rapid Development of Polyether Ether Ketone", CNCIC Chemdata Inc., 2004, 2 pages.

Green, "Body Building—Medical Materials for Systems and Scaffolding," Materials World, Journal of the Institute of Materials, vol. 10, No. 2, 2001, 4 pages.

Green, "Effects of Gamma Sterilisation on Implant Grade Polyetheretherketone," Invibio Inc., Lancashire, United Kingdom, undated, 1 page.

Green, "In Vivo Biostability Study on Polyaryletheretherketone Biomaterial," Invibio Inc., Lancashire, United Kingdom, undated, 2 pages.

Green, et al., "A Polyaryletherketone Biomaterial for Use in Medical Implant Applications," Lancashire, United Kingdom, 2001, 1 page.

Green, et al., "Polyetheretherketone Polymer and Compounds for Surgical Applications," Lancashire, United Kingdom, undated, 9 pages.

Green, Stuart, "PEEK-Optima Polymer in the Implantable Medical Device Industry," Invibio Inc., Lancashire, United Kingdom, undated, 2 pages.

Invibio, Biomaterials Solutions, "High Performance PEEK-Optima Biocompatible Polymer Chosen for Dental Abutment Healing Caps," Invibio Inc, Lancashire, United Kingdom, undated, 1 page.

Invibio, Biomaterials Solutions, "High Performance PEEK-Optima Biocompatible Polymer Chosen for New Generation Heart. Valve," Invibio Inc., Lancashire, United Kingdom, undated, 1 page.

Invibio, Biomaterials Solutions, "PEEK-Classix," Invibio Inc., Lancashire, United Kingdom, 2003, 2 pages.

Invibio, Biomaterials Solutions, "PEEK-Optima Polymer: Performance Purity Flexibility Endurance," Invibio Inc., Lancashire, United Kingdom, 2004, 3 pages.

Invibio, Biomaterials Solutions, "PEEK-Optima, Composite Hip," Invibio Inc., Lancashire, United Kingdom, undated, 2 pages.

Invibio, Biomaterials Solutions, "PEEK-Optima, Spiked Washers," Invibio Inc., Lancashire, United Kingdom, undated, 1 page.

Tangram Technology Ltd., "Polymer Data File: Polyether Ether Keotone-PEEK," Available at http://www.tangram.co.uk/TI-Polymer-PEEK.html; 2001, 5 pages.

Web pages, http://www.brainlab.com, Apr. 2, 2002; 5 pp.

"New Minimally Invasive Techniques, Improve Outcome of Spine Surgeries", Medtronic Sofamor Danek.

International Preliminary Examination Report for PCT Application Serial No. PCT/US03/05086 mailed Dec. 23, 2003.

Canadian Office Action dated Aug. 13, 2008, issued in co-pending Candian Application No. 2,475,200.

Office Action dated Jan. 22, 2009, issued in U.S. Appl. No. 11/283,006.

Amendment and Response to Office Action filed Jun. 22, 2009, in U.S. Appl. No. 11/283,006.

Office Action dated Dec. 1, 2008, issued in Canadian Application No. 2415072.

Office Action dated Jun. 19, 2009, issued in Chinese Application No. 200680030105.5.

Office Action dated Jul. 15, 2009, issued in Canadian Application No. 2475200.

Office Action dated Sep. 22, 2009, issued in European Application No. 03733832.4.

Amendment & Response to Office Action filed Jun. 3, 2009, in U.S. Appl. No. 11/458,629.

Office Action dated Feb. 5, 2009, in U.S. Appl. No. 11/458,629.

Office Action dated Aug. 11, 2009, in U.S. Appl. No. 11/223,530.

Office Action dated Aug. 21, 2008, issued in Australian Application No. 2006200772.

Notice of Allowance and Approved Claim Set dated Mar. 20, 2009, issued in Australian Application No. 2006200772.

Supplemental Search Report dated May 25, 2009, issued in European Application No. 03733832.4.

Office Action dated Mar. 31, 2009, issued in Japanese Application No. 2003-572434.

Supplemental Search Report dated Jun. 10, 2008, issued in European Application No. 04758814.0.

Office Action dated Aug. 29, 2008, issued in European Application No. 04758814.0.

Response to Office Action dated Aug. 29, 2008, filed in European Application No. 04758814.0.

Supplemental Search Report dated Mar. 24, 2009, issued in European Application No. 06785447.1.

International Search Report dated Feb. 11, 2005, issued in Application No. PCT/US2004/010277.

Written Opinion dated Feb. 11, 2005, issued in Application No. PCT/US2004/010277.

International Preliminary Report dated Oct. 27, 2005, issued in Application No. PCT/US2004/010277.

Written Opinion dated Oct. 14, 2005, issued in Application No. PCT/US2003/014615.

International Preliminary Examination Report dated Jan. 10, 2006, issued in Application No. PCT/US2003/014615.

International Preliminary Report dated Jan. 10, 2008, issued in Application No. PCT/US2006/024491.

International Search Report dated Sep. 25, 2007, issued in Application No. PCT/US2006/024491.

Written Opinion dated Sep. 25, 2007, issued in Application No. PCT/US2006/024491.

Notification of Reasons of Refusal issued in Korean Application No. 10-2005-7018906.

Notification of Decision to Grant Korean Application No. 10-2005-7018906.

Office Action dated Dec. 16, 2008, issued in Japanese Application No. 2006-509659.

Office Action dated Feb. 28, 2007, issued in Canadian Application No. 2520741.

Office Action dated Jan. 19, 2007, issued in Chinese Application No. 200480014833.8.

Office Action dated Dec. 5, 2008, issued in Chinese Application No. 200480014833.8.

Notice of Allowance dated Jun. 1, 2005, issued in U.S. Appl. No. 10/406,895.

Examiner's First Report dated Mar. 27, 2007, issued in Australian Application No. 2004228019.

Examiner's First Report dated Oct. 17, 2007, issued in Australian Application No. 2003228960.

Office Action dated Aug. 24, 2007, issued in U.S. Appl. No. 10/435,330.

Office Action dated Jan. 11, 2005, issued in U.S. Appl. No. 10/435,330.

Amendment and Response to Office Action filed Feb. 5, 2005, in U.S. Appl. No. 10/435,330.

Office Action dated May 5, 2005, issued in U.S. Appl. No. 10/435,330.

Amendment and Response to Office Action filed Aug. 5, 2005, in U.S. Appl. No. 10/435,330.

Office Action dated Aug. 28, 2006, issued in U.S. Appl. No. 10/435,330.

Amendment and Response to Office Action filed Dec. 28, 2006, in U.S. Appl. No. 10/435,330.

Office Action dated Mar. 27, 2007, issued in U.S. Appl. No. 10/435,330.

Amendment and Response to Office Action filed May 29, 2007, in U.S. Appl. No. 10/435,330.

Office Action dated Apr. 16, 2008, issued in U.S. Appl. No. 10/435,330.

Amendment and Response to Office Action filed Jul. 8, 2008, in U.S. Appl. No. 10/435,330.

Office Action dated Oct. 28, 2008 issued in U.S. Appl. No. 10/435,330.

Amendment and Response to Office Action filed Apr. 27, 2009, in U.S. Appl. No. 10/435,330.

Amendment and Response to Office Action filed Feb. 28, 2005, in U.S. Appl. No. 10/406,895.

Office Action dated Feb. 23, 2009, issued in U.S. Appl. No. 11/669,015.

Amendment and Response to Office Action filed Jul. 23, 2009, in U.S. Appl. No. 11/669,015.

Examiner's Interview Summary dated Jul. 9, 2009, issued in U.S. Appl. No. 11/669,015.

Office Action dated Aug. 17, 2004, issued in U.S. Appl. No. 10/406,895.

Amendment and Response to Office Action filed Sep. 17, 2004, in U.S. Appl. No. 10/406,895.
Office Action dated Dec. 13, 2004, issued in U.S. Appl. No. 10/406,895.
Supplemental Notice of Allowability dated Oct. 13, 2005, issued in U.S. Appl. No. 10/406,895.
Office Action dated May 7, 2009, issued in Japanese Application No. 2004-502799.
Office Action dated Aug. 29, 2008, issued in European Application No. 04758814.0.
Office Action dated Feb. 5, 2009, issued in U.S. Appl. No. 11/458,629.
Amendment and Response to Office Action filed Jun. 3, 2009, in U.S. Appl. No. 11/458,629.
Office Action dated Sep. 20, 2002, issued in U.S. Appl. No. 09/898,478.
Amendment and Response to Office Action filed Jan. 21, 2003, in U.S. Appl. No. 09/898,478.
Supplemental Amendment and Response to Office Action filed Mar. 4, 2003, in U.S. Appl. No. 09/898,478.
Fax from Examiner dated Mar. 13, 2009, issued in U.S. Appl. No. 09/898,478.
Second Supplemental Amendment and Response to Office Action filed Mar. 31, 2003, in U.S. Appl. No. 09/898,478.
Office Action dated Jun. 18, 2003, issued in U.S. Appl. No. 09/898,478.
Amendment and Response to Election Requirement filed Jul. 17, 2003, in U.S. Appl. No. 09/898,478.
Final Office Action dated Oct. 7, 2003, issued in U.S. Appl. No. 09/898,478.
Notice of Allowance dated Nov. 26, 2003, issued in U.S. Appl. No. 09/898,478.
Amendment After Final Office Action filed Nov. 12, 2003, in U.S. Appl. No. 09/898,478.
Interview Summary dated Nov. 7, 2003, issued in U.S. Appl. No. 09/898,478.
Office Action dated Oct. 5, 2006, issued in U.S. Appl. No. 10/776,094.
Amendment and Response to Office Action filed Feb. 5, 2007, in U.S. Appl. No. 10/776,094.
Office Action dated Apr. 26, 2007, issued in U.S. Appl. No. 10/776,094.
Amendment and Response filed Jul. 26, 2007, in U.S. Appl. No. 10/776,094.
Office Action to Office Action dated Oct. 12, 2007, issued in U.S. Appl. No. 10/776,094.
Amendment and Response filed Feb. 12, 2008, in U.S. Appl. No. 10/776,094.
Final Office Action to Office Action dated Apr. 23, 2008, issued in U.S. Appl. No. 10/776,094.
Amendment and Response to Office Action filed Aug. 25, 2008, in U.S. Appl. No. 10/776,094.
Office Action dated Nov. 14, 2008, issued in U.S. Appl. No. 10/776,094.
Amendment and Response to Office Action filed Feb. 13, 2009, in U.S. Appl. No. 10/776,094.
Office Action dated May 22, 2009, issued in U.S. Appl. No. 10/776,094.
Amendment and Response to Office Action filed Jul. 31, 2009, in U.S. Appl. No. 10/776,094.
Office Action dated Mar. 28, 2006, issued in U.S. Appl. No. 10/776,094.
Amendment and Response to Office Action filed Jun. 28, 2006, in U.S. Appl. No. 10/262,574.
Notice of Allowability dated Sep. 18, 2006, issued in U.S. Appl. No. 10/262,574.
Amendment After Allowance filed Dec. 18, 2006, in U.S. Appl. No. 10/262,574.
International Preliminary Examination Report dated Jan. 20, 2004, issued in Application No. PCT/US2002/031201.
Response to Written Opinion filed Oct. 13, 2001, in Application No. PCT/US2002/031201.
International Search Report dated Mar. 3, 2005, issued in Application No. PCT/US2004/005751.
Written Opinion dated Mar. 3, 2005, issued in Application No. PCT/US2004/005751.
International Preliminary Examination Report dated Mar. 3, 2005, issued in Application No. PCT/US2004/005751.
International Search Report dated Sep. 13, 2001, issued in Application No. PCT/US2001/021205.
Written Opinion dated Jun. 10, 2002, issued in Application No. PCT/US2001/021205.
International Preliminary Examination Report dated Apr. 23, 2003, issued in Application No. PCT/US2001/021205.
International Preliminary Examination Report dated Dec. 23, 2003, issued in Application No. PCT/US2003/005086.
Office Action dated May 27, 2008, issued in Japanese Application No. 2003-530164.
Notice of Allowance dated Dec. 24, 2008, issued in Japanese Application No. 2003-530164.
Office Action dated Nov. 21, 2008, issued in Australian Application No. 2004216131.
Office Action dated May 13, 2008, issued in U.S. Appl. No. 11/069,390.
Amendment and Response to Office Action filed Sep. 15, 2008, in U.S. Appl. No. 11/069,390.
Final Office Action dated Dec. 24, 2008, issued in U.S. Appl. No. 11/069,390.
Amendment and Response to Office Action filed Feb. 24, 2009, in U.S. Appl. No. 11/069,390.
Office Action dated May 18, 2009, issued in U.S. Appl. No. 11/069,390.
Amendment and Response to Office Action filed Jul. 28, 2009, in U.S. Appl. No. 11/069,390.

* cited by examiner

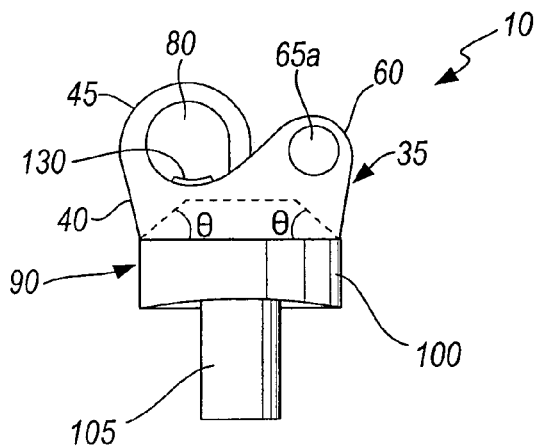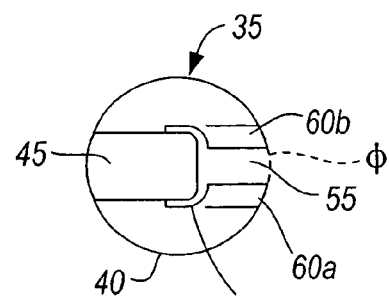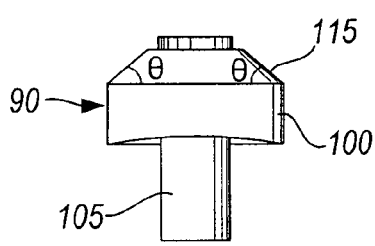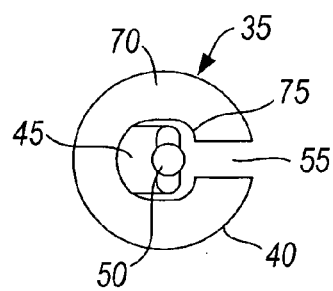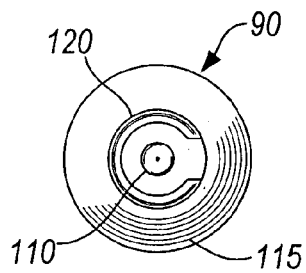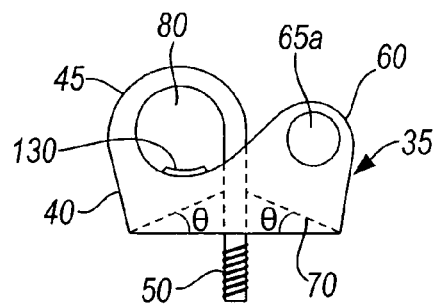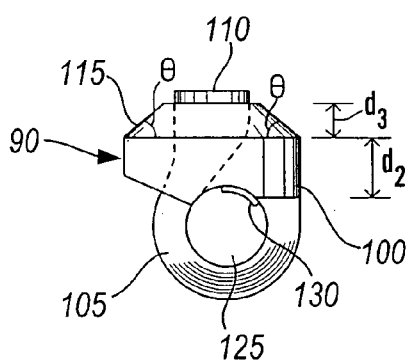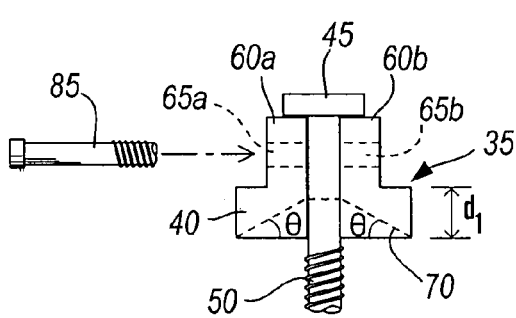
FIG. 1
FIG. 2A
FIG. 2B
FIG. 2C
FIG. 2D
FIG. 3A
FIG. 3B
FIG. 3C

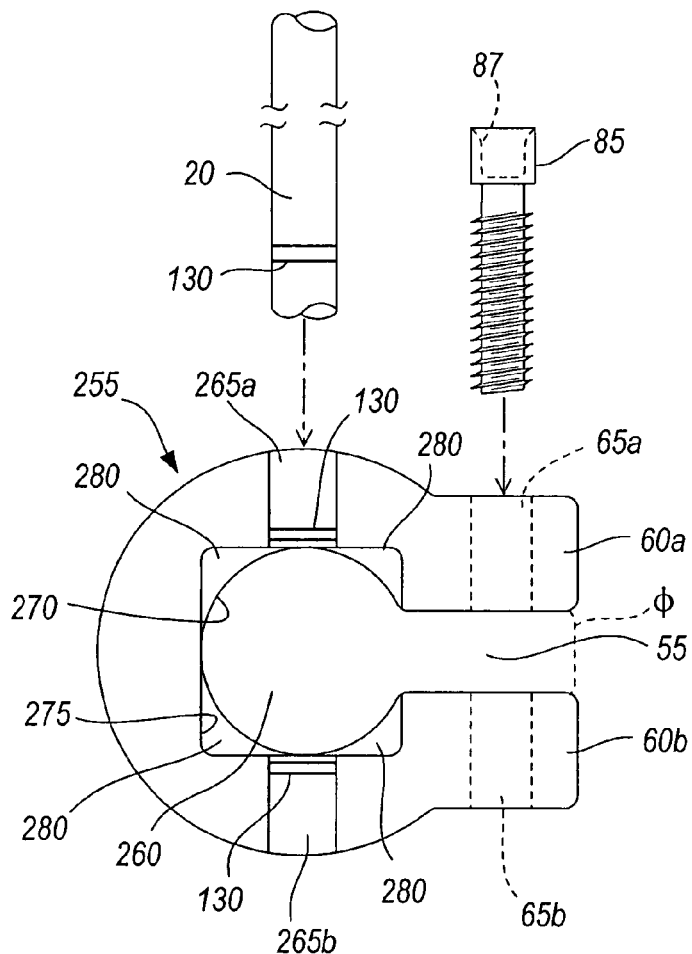
FIG. 16
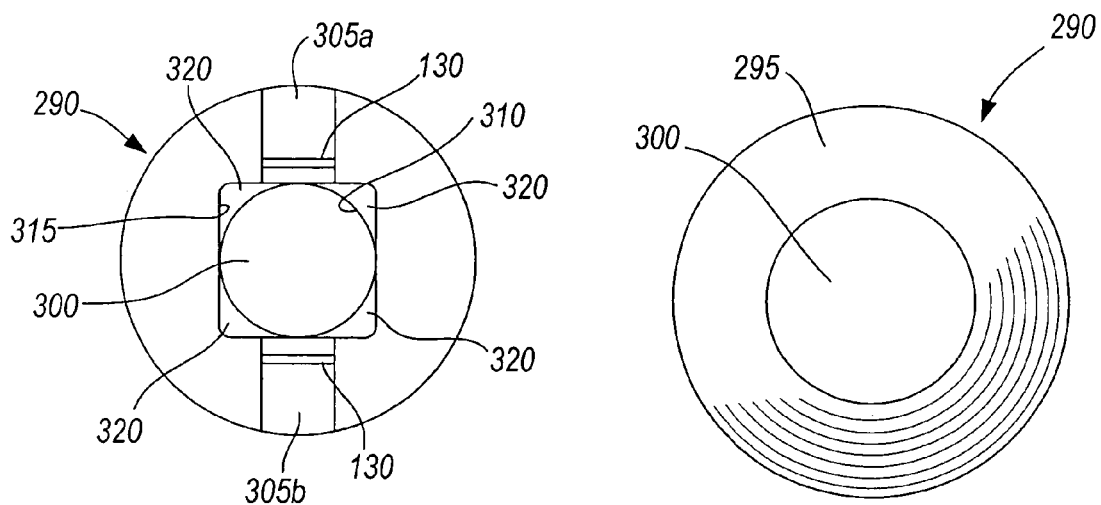
FIG. 17A  FIG. 17B

PEDICLE SCREW CONNECTOR APPARATUS AND METHOD

CROSS-REFERENCE TO RELATED APPLICATIONS

Priority is claimed from U.S. Provisional Patent Application No. 60/359,246 filed Feb. 20, 2002 entitled "PEDICLE SCREW CONNECTOR APPARATUS AND METHOD," which is incorporated by reference in its entirety.

FIELD OF THE INVENTION

This invention relates generally to securement devices and, more particularly, to a coupling and locking mechanism that is used to secure two rods together, or to secure a rod to one or more pedicle screws.

BACKGROUND OF THE INVENTION

Spinal fusion surgery is a method of placing bone graft material between two mobile segments of the spine to knit them together as one unit and eliminate motion between the segments. Fusion surgery can be performed with or without the use of spinal instrumentation for internal fixation. Internal fixation instruments are used to provide stability to decrease motion between segments of the spine and to allow the bone fusion to knit together. They act as an internal splint. Internal fixation devices may be attached with hooks, wires or bone screws. When bone screws orpedicle screws are employed they are screwed into the pedicles of a vertebra and connected to rods or plates to stabilize movement between the vertebrae to which they are connected. Thus, pedicle screws are implants used in the thoracic and lumbar spine to help surgeons stabilize the spine. "Headless" pedicle screws are used for several reasons, including the fact that headless screw design has been known to make it easier for surgeons to implant pedicle screws while avoiding the facet joint. In addition, pedicle screws can be implanted at each spinal level.

One such headless pedicle screw is the screw associated with TSRH-3D™ manufactured by Medtronic Sofamor Danek. More particularly, the present invention is capable of working in conjunction with "bolt 88" disclosed in U.S. Pat. Nos. 5,643,263 and 5,885,285 to Simonson. The present invention is a replacement for the clamp found in U.S. Pat. Nos. 5,643,263 and 5,885,285 to Simonson, the disclosures of which are specifically incorporated into this specification by reference. Details of the TSRH spinal implant system are disclosed in the "Surgical Technique Manual" provided by Danek Medical, Inc., published in 1990, which disclosure is also incorporated herein by reference.

The use of fixation devices for the treatment of vertebrae deformities and injuries is well known in the art. Various fixation devices are used in medical treatment to correct curvatures and deformities, treat trauma and remedy various abnormal spinal conditions. Treatment of these conditions generally requires the implantation of various component pieces such as support rods, crosslinks, caudal facing hooks, cranial facing hooks and like components, which form a spinal implant system.

It is necessary in spinal implant systems to properly anchor the system to bone to provide necessary support of the implant. Bone screws are commonly used for anchoring spinal implant systems. There are, however, several problems with the use of fixed screws for anchoring spinal implants. The exact final position of a bone screw is difficult, if not impossible, to predict prior to the exposure of the patient's bone. This unpredictability results from the uncertainty of exact bone formation and shape within an individual patient. Additionally, it can be difficult to predetermine the structure of the bone, i.e. whether the bone is soft or even osteoporotic. Even if the final position of the screw can be predetermined, the necessary shape and position of a spinal rod implant may create unwanted stress upon the bone screw or the bone itself. This is especially true where a plurality of screws is required along the spinal column for securement of an implant. The alignment of the rod with several screws along the vertebrae compounds this problem and makes undesired stress much more probable. Moreover, this misalignment may influence the extent and speed of correction of the spinal defect.

With regard to the size of a bone screw and connector, a low profile arrangement provides less disruption of the tissues in the vicinity of the spine. Nonetheless, it is common in the insertion of spinal implants to necessarily remove portions of vertebral bone to allow proper insertion of a bone screw. Moreover, current systems in use may result in long-term muscular displacement that may lead to a patient's pain or discomfort. Thus, a low profile bone screw and connector offers advantages, including less post-operative pain and discomfort for the patient.

Increased complexity of the installation procedure is undesirable because it increases a patient's time in surgery. Increased operating time is known to increase the risk of many complications associated with surgery. The additional time necessary to remove, or even temporarily dislocate, bone or muscular tissue also increases operating time, and thus the risk of complications.

In view of the above, there is a long felt but unsolved need for a method and system that avoids the above-mentioned deficiencies of the prior art and that provides an effective system that is relatively simple to employ and requires minimal displacement or removal of bodily tissue.

SUMMARY OF THE INVENTION

In accordance with the present invention, a low-profile connector device is provided for attaching two cylindrical objects or rods together, such as a spinal rod implant and the shaft of a pedicle screw used in spinal stabilization surgeries. The present invention is a variable angle connector that allows single point clamping. More particularly, after the rods are inserted into the receptacles of the connector, they may be moved longitudinally within the receptacles, and they may be rotated within the receptacles. Furthermore, in at least one embodiment of the present invention, approximately 60 degrees of rotational freedom exists for adjusting the connector to accommodate the position of the rods, thus allowing for motion to manipulate the assembly and to adjust the location of the connector and rods to their pre-final position. Subsequently, a single tightening screw is advanced within the connector to secure all degrees of freedom. The action of the tightening screw on the connector creates forces within the connector that secure and fixedly interconnect both of the rods within the connector, thus setting the connector and the rods in an interlocked final position.

In a first aspect of the invention, a connector is presented for securing two rods. The connector comprises a body including a first substantially conical surface having a slit and opposing joining sections adjacent the slit. In addition, the connector includes first and second receptacles for receiving first and second rods, respectively. The connector also includes a second substantially conical surface that is operatively associated with the first substantially conical surface. Finally, the connector includes means for urging the joining sections toward each other. Tension force is created within the connector upon urging the opposing joining sections in closer proximity because narrowing the slit reduces the diameter of the first substantially conical surface, which in turn pushes down on the second substantially conical surface. The tension force causes the two rods to be secured within the connector's receptacles because the receptacles create constricting or compressive forces around the rods. As an example of use in spinal surgery, one rod may take the form of a shaft of a pedicle screw, while the other rod is a stabilization rod that bridges a problematic spinal disc. The connector may be of unitary or one-piece construction, or it may be formed of a plurality of parts, such as two-part construction. In a preferred embodiment, the receptacles are formed of bands that are interconnected.

In a second aspect of the invention, a two-member connector is presented for securing two rods. Here, the connector includes a first member having a first receptacle for one of the rods, a first substantially conical surface having a slit and opposing joining sections adjacent the slit. The connector also has a second member that includes a second receptacle for a second rod, and a second conical surface for contacting the first conical surface. Finally, the connector includes means for forcing the joining sections toward each other, wherein the two rods are secured within the connector upon forcing the joining sections toward each other.

In yet a separate aspect of the invention, a connector for securing two rods is presented. The connector includes a first member having an interior substantially conical surface having a slit and adjacent opposing joining sections. The first member also has a first rod band at least partially disposed through a center opening in the first member. In addition, the connector has a second member including an exterior substantially conical surface and a second rod band that is also at least partially disposed through a central opening in the second member. Means for interconnecting the first rod band to the second rod band are provided, such as by threading the two bands together. In addition, means for forcing the opposing joining sections toward each other are also provided, such as by using a threaded tightening screw.

In yet a separate aspect of the invention, an end connector is provided that utilizes an end position on the end of a rod to form at least a portion of the connector of the present invention. The end connector includes two substantially conical surface members where one of the conical surfaces is formed as an integral part of the end of the rod. Among other things, this aspect of the invention allows for further controlling the eccentricity of the connector, as well as reducing the size of the connector because a second receptacle or rod band is not necessary given that the rod is already connected to the end connector. The end connector functions in a manner similar to the other connectors described herein. More particularly, a slit along the first substantially conical surface is narrowed by using a tightening screw to pull the two opposing joining sections of the slit toward each other. This ultimately results in creating a compression force around the rod band that holds the pedicle screw, thereby securing the pedicle screw to the rod.

In yet a separate aspect of the invention, a connector is provided that includes a plurality of pieces, and more particularly, a connector having four pieces is described. The four-piece connector includes first and second rod receiving members, and first and second substantially conical surface members. One of the conical surface members includes a slit and opposing joining sections adjacent the slit. Means for urging the joining sections toward each other is also provided, such as a tightening screw. The rod receiving members force the rods inserted therein to impinge upon the conical surface members, thereby securing the rods within the connector.

In yet a separate aspect of the present invention, a method of securing a pedicle screw to a stabilizing rod is presented. The method includes several steps, including inserting the exposed shaft of the pedicle screw and the rod into a connector having a first substantially conical surface that has a slit and opposing joining sections adjacent the slit. The connector also has first and second receptacles for receiving the rod and the shaft of the pedicle screw. In addition, the connector includes a second substantially conical surface that at least partially contacts the first substantially conical surface. Additional steps include inserting a tightening screw into the openings of the joining sections, and tightening the tightening screw to force the joining sections together and thus constricting the first substantially conical surface of the first member. The tightening step decreases the diameter of the first substantially conical surface, which pushes against the second substantially conical surface and thereby creates a constricting force around the rod and the shaft of the pedicle screw through the receptacles.

In a separate aspect of the invention, a projection or surface texturing may be provided within a receptacle or rod band of the connector, and also potentially provided on the shaft of the screw or the rod to provide additional stability to the assembly.

Based on the foregoing summary, a number of worthwhile aspects of the present invention can be readily identified. The minimal size of the connector device allows attachment of the device to human bone without significant displacement of human tissue. Therefore, the complexity of surgery and the following pain and discomfort of the patient may be minimized. The nature of the device, combined with its small size and profile, may allow a surgeon to attach the securement device to a secure portion of the human body without the need to remove bony processes which may be necessary to accommodate a larger attachment device. The simplicity of the elements, and the assembly process thereof reduces the training and experience or surgeons necessary to achieve desired results, and, may reduce the patient's time in surgery, thus reducing the risk and probability of surgical complications. Finally, a number of embodiments of the present invention may be used in combination to allow a surgeon great latitude in the selection of materials used. The surgeon may select from different embodiments of the connector to best fit the surgical implant parameters. With these choices, the surgeon may then best determine which embodiments of which elements to select to minimize removal or displacement of bodily tissue or bone, and thereby reduce both the patient's risk of surgical complications and post-surgical pain and discomfort.

A significant feature of the present invention is the ability to provide a construct used to stabilize the spine or a portion thereof. This is a very low profile configuration (as compared to existing devices) that minimizes the length of the incision that is necessary to perform the surgery. Furthermore, a mechanical advantage is gained by the interaction of the components as previously described. Specifically, strength of the final connection is not simply attributable to the tightening of the tightening screw, but is also attributable, in part, to the placement of the spinal rod or screw shaft within the receptacles of the connector, and the wedge like interaction of the conical surfaces of the connector.

Additional advantages of the present invention will become readily apparent from the following discussion, particularly when taken together with the accompanying drawings.

BRIEF DESCRIPTION OF THE DRAWINGS

FIG. 1 is a side elevation view of a first embodiment of the present invention;

FIG. 2A is a is a top view of a first member of a two-piece connector;

FIG. 2B is a bottom view of the first member shown in FIG. 2A;

FIG. 2C is a side elevation view of the first member shown in FIG. 2A;

FIG. 2D is a second side elevation view of the first member shown in FIG. 2A;

FIG. 3A is a side elevation view of a second member of a two-piece connector;

FIG. 3B is a bottom view of the second member shown in FIG. 3A;

FIG. 3C is a second side elevation view of the second member shown in FIG. 3A;

FIG. 16 is a top view of a component of the four-piece connector shown in FIG. 15;

FIG. 17A is a bottom view of a separate component of the four-piece connector shown in FIG. 15;

FIG. 17B is a top view of the component shown in FIG. 17A;

DETAILED DESCRIPTION OF THE PREFERRED EMBODIMENT

Figure 4:
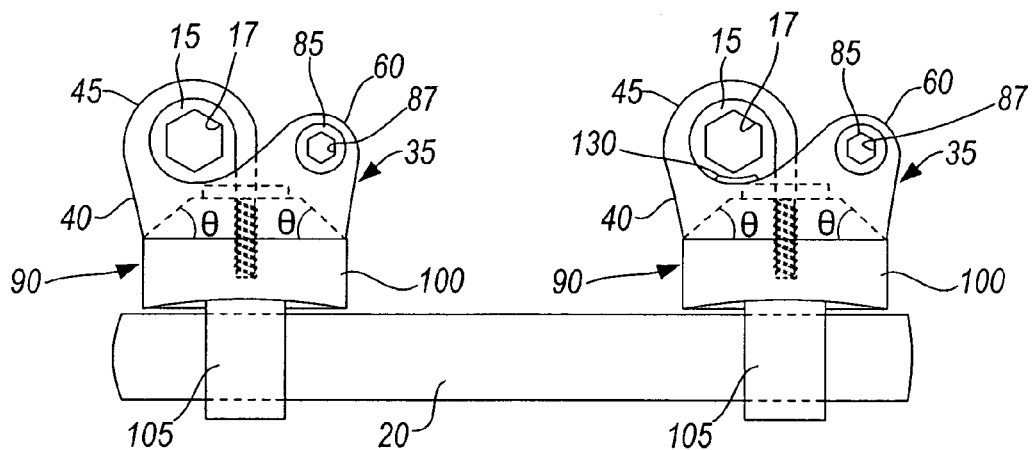
FIG. 4 is a plan view of two connectors used to connect pedicle screws to a stabilizing rod.

Referring to FIG. 1, a first embodiment of the connector of the present invention is shown. The connector 10 includes a first rod band 45 and a second rod band 105. In addition, the connector includes substantially conical surfaces within the interior of the connector. Finally, the connector includes a slit and a means for drawing together the adjacent joining sections of the slit, thereby decreasing the diameter of the upper conical surface that in turn forces the lower conical surface downwards, thereby tightening the bands 45 and 105. The bands may be tightened around two rods, such as a vertebrae stabilizing rod and the shank of a pedicle screw. Various embodiments of the invention will be described below.

Referring now to FIGS. 2A-3C, a first embodiment of the connector 10 of the present invention is shown, wherein the connector is formed of two pieces. However it is to be understood that the present invention may be of unitary construction, or it may be constructed of a plurality of pieces, such as three or four pieces, as will be discussed below.

In a first embodiment, connector 10 utilizes two-piece construction, wherein the first piece is first member 35. First member 35 shown in FIGS. 2A-2D includes a first body 40, first rod band 45, first band fitting 50, slit 55, opposing joining sections 60a and 60b, openings 65a and 65b, interior substantially conical surface 70, and center body opening 75. As can be seen in the figures, the various substantially conical surfaces may be truncated, thereby allowing for passage of other structure, such as the band fittings. Accordingly, as used herein, the term "substantially conical surface" includes a substantially truncated conical surface. First body 40 is preferably circular, although its exterior surface may be other shapes, such as square, rectangular, or a multi-side polyhedron. One end of first rod band 45 is connected to first body 40. First rod band 45 forms a loop along its length, thereby creating an opening or a first rod position 80. As first rod band 45 curves, it is disposed through center body opening 75 and extends below interior substantially conical surface 70. At the end of the portion of first rod band 45 that is disposed through center body opening 75 is first band fitting 50. First band fitting 50 is preferably an interconnection device that allows first member 35 to be interconnected to the second piece of connector 10, as will be discussed below. First band fitting 50 includes interconnection means, such as threads, a hook, or a socket, that receives, or is received in, the second piece of connector 10. Joining sections 60a and 60b are adapted to provide means for pulling joining section 60a toward joining section 60b. Preferably, joining sections 60a and 60b include openings 65a and 65b, respectively, that receivingly accept a tightening screw 85. When connector 10 is installed, as will be discussed below, tightening screw 85 is placed through openings 65a and 65b and is tightened to bring joining section 60a closer to joining section 60b. More particularly, due to the presence of slit 55 in first body 40 between joining sections 60a and 60b, tightening screw 85 is used to pull joining section 60a toward joining section 60b.

Referring now to FIGS. 3A through 3C, the second member 90 of connector 10 is illustrated. Second member 90 includes a second body 100, second rod band 105, second rod band fitting 110, exterior substantially conical surface 115, and second central body opening 120. Second body 100 is preferably circular, although its exterior surface may be other shapes, such as square, rectangular, or a multi-side polyhedron, as long as the upper exterior surface is substantially conical, that is, exterior substantially conical surface 115. One end of second rod band 105 is interconnected to body 100. Second rod band 105 forms a loop along its length, thereby creating an opening or a second rod position 125. As second rod band 105 curves, it is disposed through or in the vicinity of center body opening 120. At the end of second rod band 105 is second band fitting 110. Similar to first band fitting 50, second band fitting 110 is preferably an interconnection device that allows first member 35 to be interconnected to second member 90. More particularly, first rod band 45 is connected to second rod band 105. Accordingly, second band fitting 110 must mate with first band fitting 50. Preferably, the interconnection means includes threads, a hook, or a socket, an expansion fitting or some type of connection that interconnects first band fitting 50 with second band fitting 110. For example, preferably first band fitting 50 may be fitted with male threads and second band fitting 110 with matching female threads. Alternately, first band fitting 50 may be fitted with a T-shaped interlocking fitting (not shown) that can be pushed into an opening in second band fitting 110 and turned 90 degrees to lock the two pieces together. Rotational freedom between rods is provided when using a threaded connection between the first rod band 45 and second rod band 105 because the threads can be partially released with the rods situated within the connector to adjust the connector to accommodate the position of the first rod (or pedicle screw shaft) relative to the second rod (or spinal stabilization rod). At least approximately 60 degrees of rotational freedom exists for moving and adjusting the rods/screw 20 and 15 relative to one another, thus allowing for motion to manipulate the assembly and to adjust the location of the connector 10 and rods/screw 20, 15 to their pre-final position. Subsequently, the tightening screw 85 can be used to interlock the rods/screws 20, 15 within the connector 10. If properly configured, this rotational adjustability would also be available if a socket type of fitting were used to make the connection between first band fitting 50 and second band fitting 110.

Referring now to FIG. 2D, the dimensions of first member 35 may be reduced, and therefore optimized, by reducing the size of its various components. For example, rounded corners may be incorporated into first body 40 to further reduce its size. In addition, the height of dimension "$d_1$" may be adjusted to reduce the overall size of first body 40, and therefore, of first member 35. The typical diameter of a pedicle screw 15 is 5 mm, and the distance between pedicle screw 15 and tightening screw 85 is about 4 mm, although this dimension will vary depending upon the size and the configuration of the connector used. The angle θ of interior substantially conical surface 70 is preferably between 15 and 75 degrees, and more preferably, between 20 and 60 degrees, and more preferably yet, between 25 and 50 degrees, and still more preferably yet, between about 30 to 45 degrees, with one preferred embodiment having an angle θ of about 30 degrees. Exterior substantially conical surface 115 is formed at an angle θ similar to that of interior substantially conical surface 70. Slit 55 is preferably formed by an open arc φ in the substantially conical surface in which it is disposed. The open arc φ is preferably between about 5 to 50 degrees, and more preferably, between about 10 to 40 degrees, and more preferably yet, between about 15 to 35 degrees, with one preferred embodiment having an angle φ of about 30 degrees.

Similarly, the dimensions of second member 90 may also be reduced, and therefore optimized, by reducing the size of its various components. For example, the height of dimension "$d_2$" of second body 100 may be adjusted to reduce the overall size of second member 90. Rounded corners may be incorporated into second body 100 to further reduce its size. In addition, exterior substantially conical surface 115 may be reduced in size by reducing its height "$d_3$" depending upon the specific application. Thus, a separate aspect of the present invention is the ability to optimize the dimensions of the connector's components, by considering the specific application at hand. Optimization techniques are applied, such as finite element analysis, to calculate the anticipated stress and strain on the various structures of the connector. Thereafter, the size of the connector can be reduced to provide the minimum profile necessary to withstand the anticipated stresses, while still maintaining a satisfactory factor of safety against structural failure for the given mode of use.

Connector 10 is assembled by operatively associating first member 35 with second member 90. Depending on the type of interconnection used between first member 35 and second member 90, and also depending upon the special constraints of the patient's particular surgical condition, first member 35 may be joined to second member 90 either before or after each member is attached to a rod or screw. In the first embodiment depicted in FIGS. 2A-3C, first band fitting 50 possesses male threads and second band fitting 110 possesses female threads. As such, first band fitting 50 is threaded into second band fitting 110, thereby connecting first member 35 to second member 90 to form connector 10. Since the threading action is not possible after insertion of a pedicle screw 15 into the patient's bone and insertion of the shank of the pedicle screw 15 into first member 35, first member 35 is preferably threaded to the second member 90 prior to inserting the shank of the pedicle screw 15 into connector 10. However, as noted above, connector 10 may be formed of one piece.

Unitary or one-piece connector construction is possible by manufacturing connector 10 such that first member 35 is interlocked with second member 90. For example, a one-piece connector 10 may be formed by welding first rod band 45 of first member 35 to second rod band 105 of second member 90. Other means for interconnecting first member 35 to second member 90 to form connector 10 are considered within the scope of the invention, such as by chemically bonding the components together, casting them as one unit, or otherwise providing a structural mechanism for interlocking the pieces together. A unitary construction would limit rotational freedom between rods, although each rod may be rotated within each receptacle or rod band before securing the rods using the tightening screw or other similar means for creating the interlocking tension and constricting forces within the connector. Alternately, a unitary construction could be used that provides rotational adjustability, such as by utilizing a permanently interlocked rotatable socket type of fitting (not shown) that is engaged during manufacture of the device.

Referring now to FIG. 2C, in a separate aspect of the invention, projections or surface texturing 130 maybe added to a portion of the interior surface of first rod band 45. Similarly, as shown in FIG. 3C, projections or surface texturing 130 may be added to a portion of the interior surface of second rod band 105. Preferably, surface texturing may take the form of ridges and grooves or arcuate shaped projections. Such a configuration of texturing allows first rod band 45 and second rod band 105 to tighten around rods 20 or screws 15 held within their respective interior regions, namely first rod position 80 and second rod position 125. These ridges and grooves are preferably positioned to provide a mating surface with the exterior surface of a rod 20 or screw 15, which may also have surface texturing 130, and which is placed within first rod position 80 and second rod position 125. Surface texturing 130, therefore, would tend to aid in preventing longitudinal motion of a rod 20 or screw 15 within first rod position 80 and/or second rod position 125. Surface texturing 130, however, is considered optional, and is not necessary for the proper functioning of connector 10.

Figure 5:
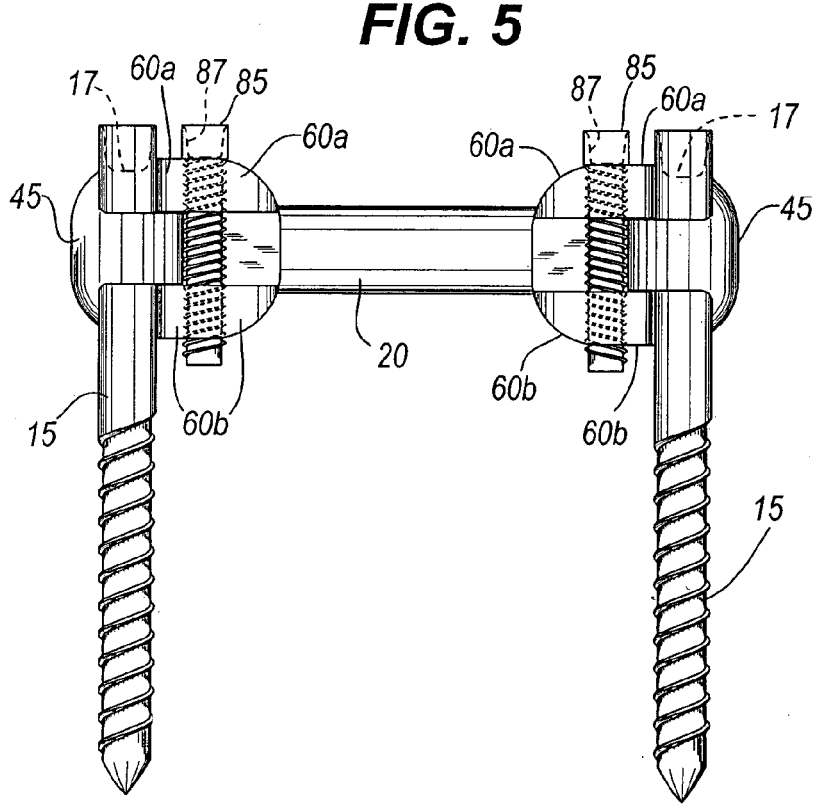
FIG. 5 is a side view of the apparatus depicted in FIG. 4.
Figure 6:
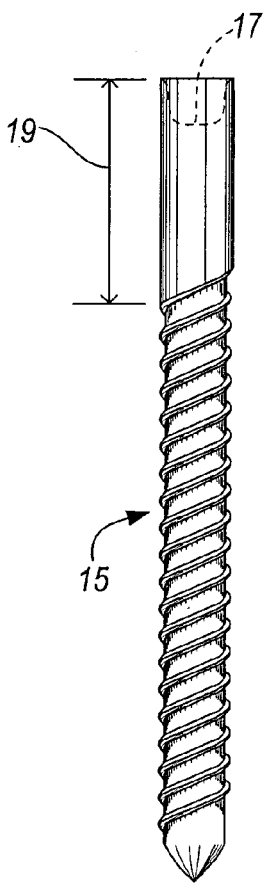
FIG. 6 is a pedicle screw known in the prior art.

Referring now to FIGS. 4 and 5, in a separate aspect of the invention, a plurality of connectors 10 may be used along a length of rod 20. The adjustable nature of the connector 10 allows the connector to be moved along the length of rod 20 prior to advancing tightening screw 85 and interlocking the connector 10 to the rod 20. As shown in FIG. 6, a pedicle screw of the prior art is illustrated. Such a pedicle screw includes a smooth shaft or shanked portion 19 that can easily be grasped by the connector 10 of the present invention.

Figure 7:
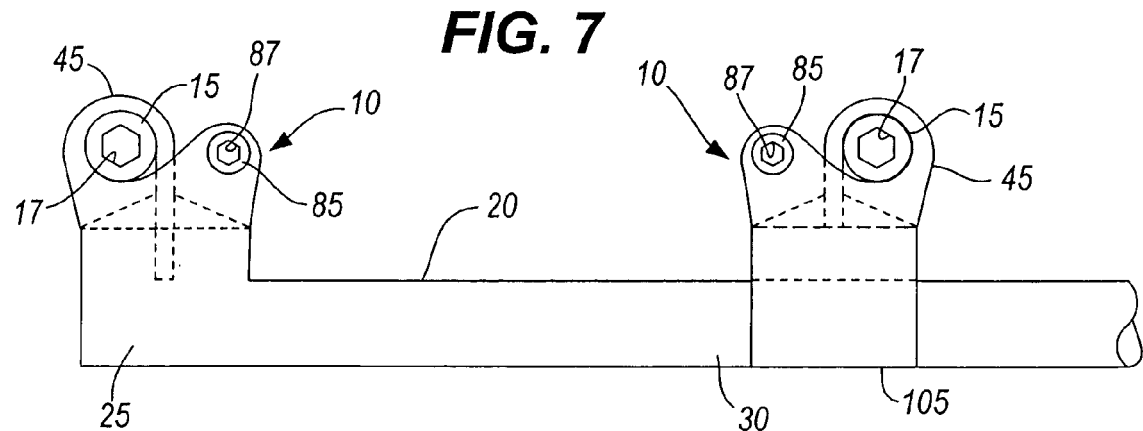
FIG. 7 is a plan view of two connectors, including an end connector formed as an integral part of a rod, wherein the connectors are used to connect pedicle screws to a stabilizing rod.
Figure 8:
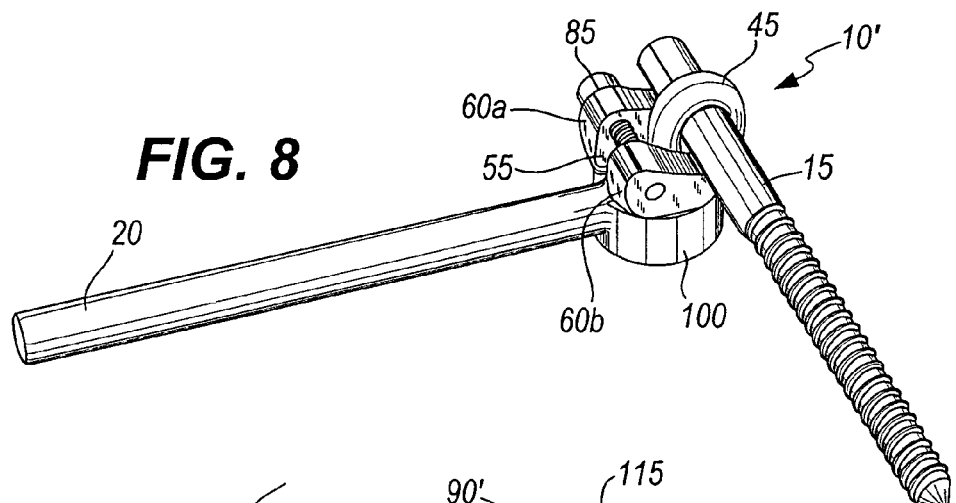
FIG. 8 is a perspective view of an end connector formed as an integral part of a rod.
Figure 9:
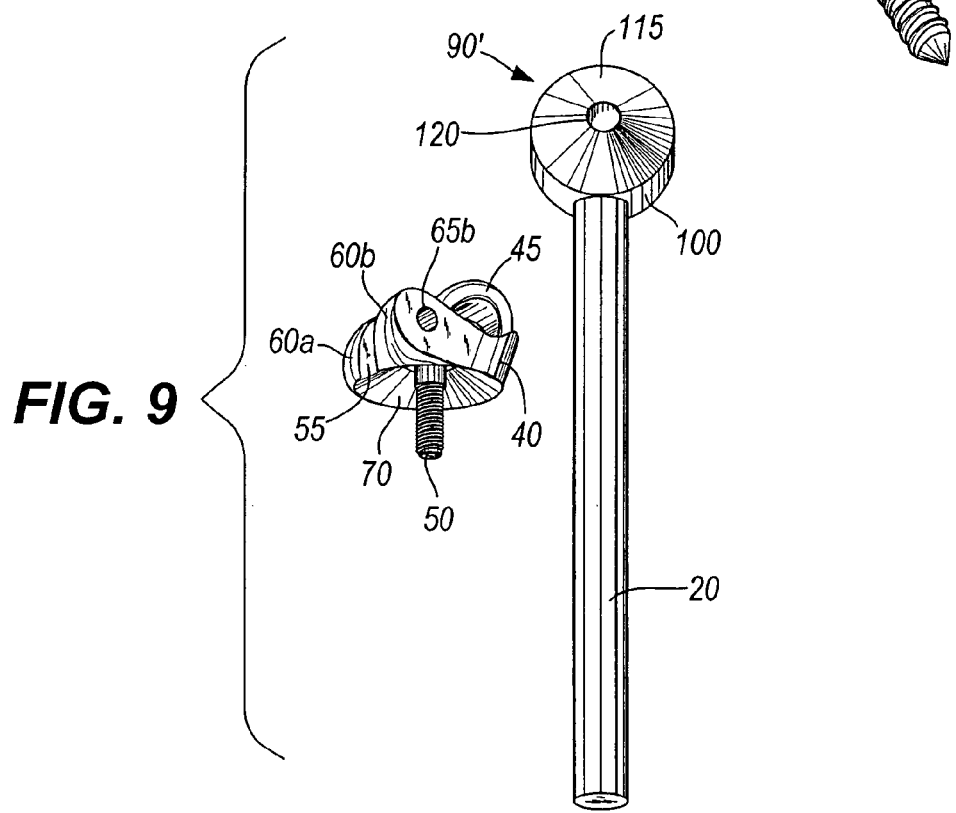
FIG. 9 is a perspective view of a two-piece end connector formed as an integral part of a rod.
Figure 10:
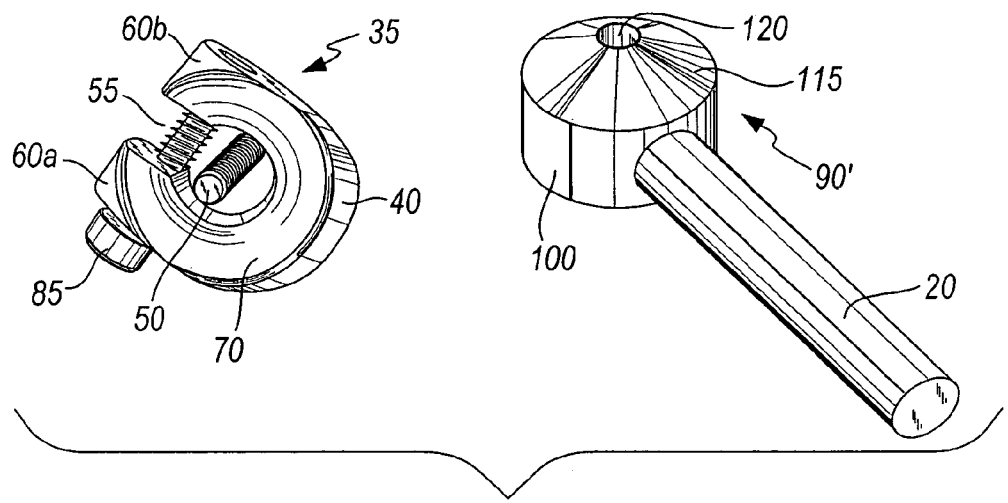
FIG. 10 is a different a perspective view than that of FIG. 9 of a two-piece end connector formed as an integral part of a rod.
Figure 11:
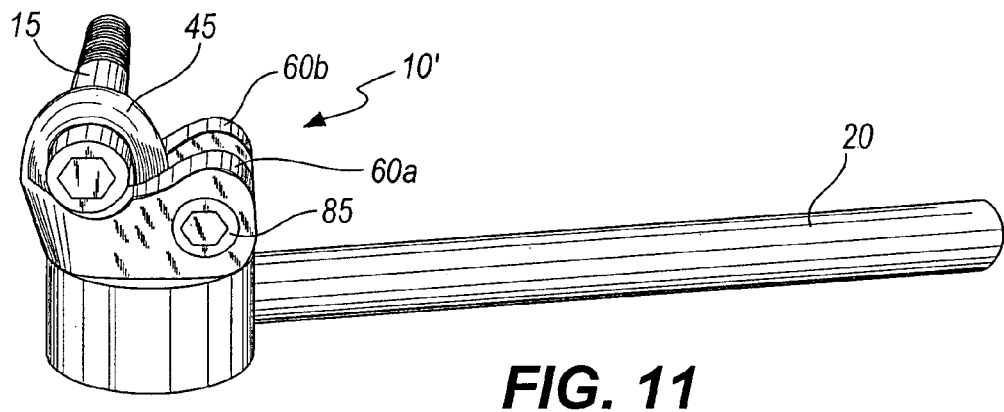
FIG. 11 is a different perspective view than that of FIG. 8 of an end connector formed as an integral part of a rod.
Figure 12:
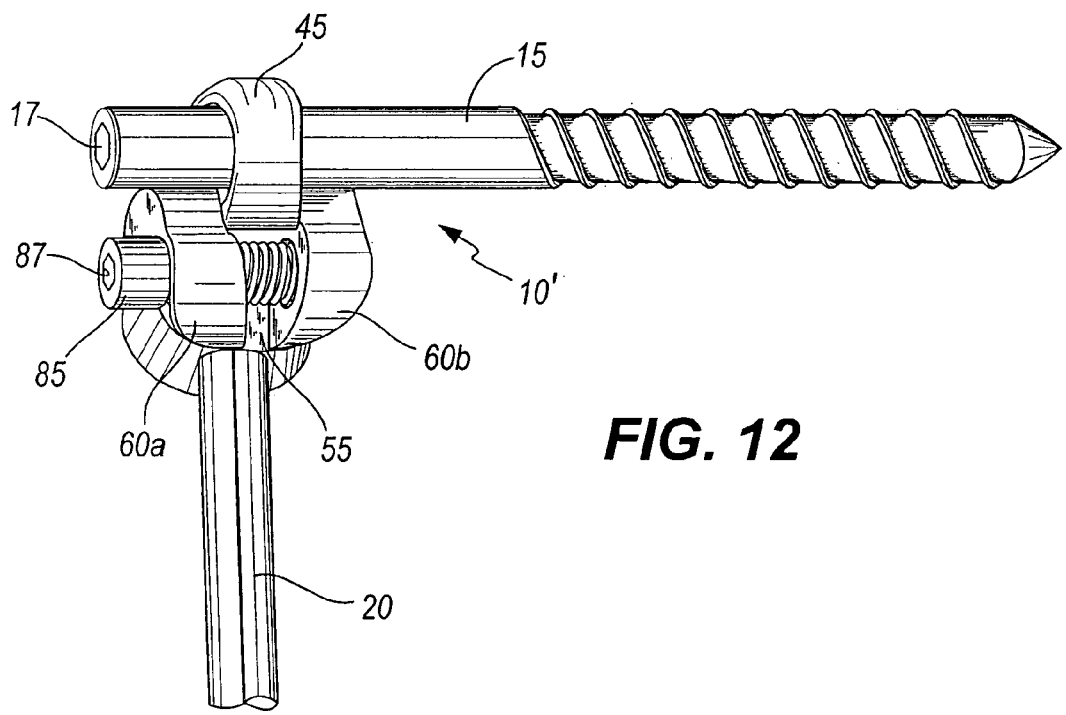
FIG. 12 is a different perspective view than that of FIGS. 8 or 11 of an end connector formed as an integral part of a rod.

In a separate aspect of the present invention, a connector having two conical surfaces may be adapted to the end of a rod 20, as shown in FIGS. 7-12. More particularly, rod 20 is manufactured with a conical surface forming an end of rod 20. For example, in the case of the embodiment referred to as connector 10, rod 20 may be manufactured with second member 90' pre-formed at the end of rod 20. Referring to FIG. 7, a connector 10' is shown at the end 25 of rod 20. In addition, a second connector 10 is shown at an interior rod location 30. Thus, the connector of the present invention may be formed as an integral part of rod 20, that is, connecter 10, or it may be a separate device that is adjustable along the length of the rod 20, as in the case of connector 10.

Referring now to FIGS. 8-12, the separate embodiment of the connector 10' formed as an integral part of rod 20 is illustrated. In this embodiment, rod 20 is continuous with end connector 10'. In an illustrative example of end connector 10', a two-piece connector 10' is shown that includes a first member 35 that is consistent in characteristics to the first member 35 of previously discussed for connector 10. However, connector 10' features a second member 90' that is formed at the end of rod 20. Here, rod 20 includes an exterior substantially conical surface 115. When assembled by threading or otherwise connecting first member 35 to second member 90', the exterior conical surface 115 of second member 90' comes in close proximity of interior substantially conical surface 70 of first member 35.

In use, the present embodiment functions similarly to the other embodiments described herein in terms of how the conical surfaces of the connector create interlocking forces. In the present embodiment, first member 35 is interlocked with rod 20 at second member 90', such as by threading. After a pedicle screw 15 is inserted into a vertebra, first rod band 45 of first member 35 is slipped over the exterior of pedicle screw 45. If necessary, the threads between the first member 35 and second member 90' can be partially released (or not fully tightened) to provide rotational adjustability to the connector 10' to accommodate the location of pedicle screw 15 and rod 20. Tightening screw 85 is then tightened to urge joining section 60a toward joining section 60b of first member 35. This action decreases the diameter of interior substantially conical surface 70, forcing exterior conical surface member 90' to move longitudinally from a first position to a second position relative to first member 35, thereby placing the first rod band 45 in a state of compression around pedicle screw 15, and therefore, interlocking the rod 20 to the pedicle screw 15.

Figure 13:
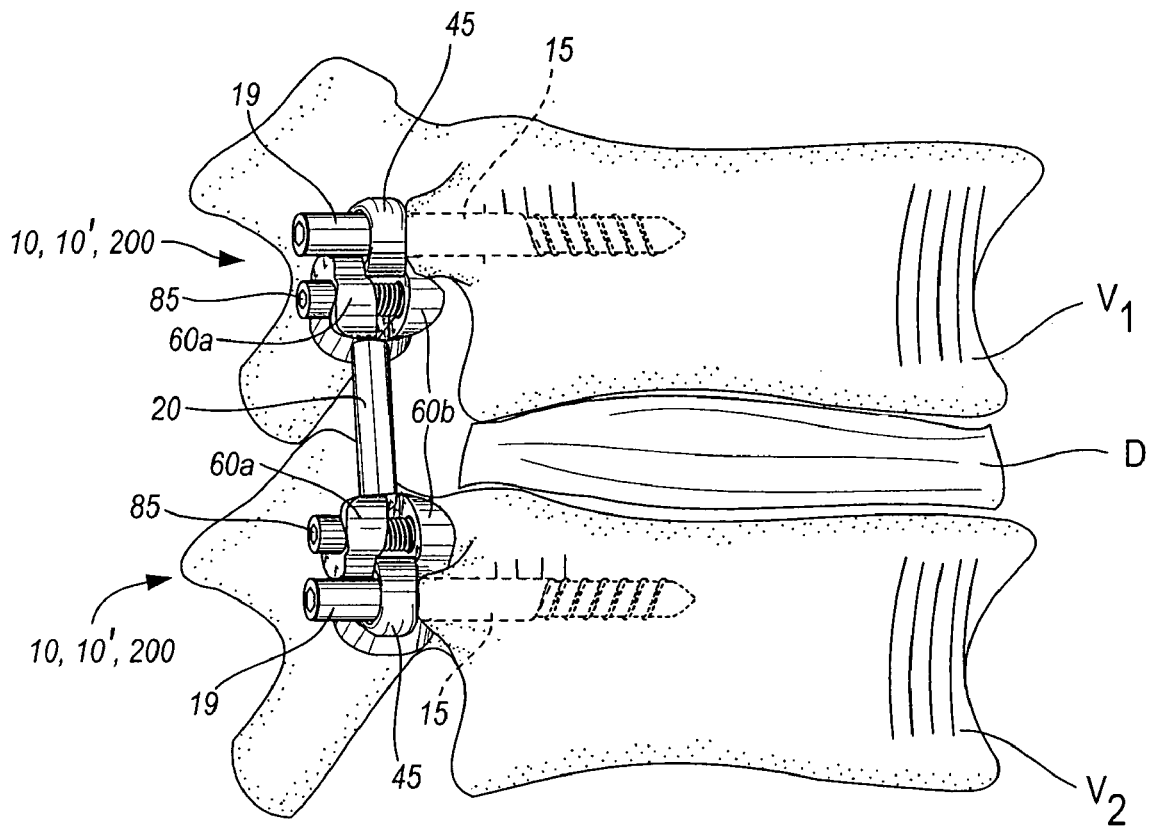
FIG. 13 is a side elevation view of two connectors of the present invention used to bridge a problematic vertebral disc.

Referring now to FIG. 13, an example of use in spinal surgery is illustrated. Here, a problematic spinal disc D is initially identified by a physician. During surgery, an incision is made through the skin and muscle overlying the implant location of the spine. Then a first pedicle screw is inserted in vertebra $V_1$ and a second pedicle screw is inserted into vertebra $V_2$. The surgeon then uses an adjustable connector, such as connector 10 and/or a rod 20 having an end connector 10'. If not of unitary construction, and if not already assembled, connector 10 is assembled by connecting first member 35 to second member 90. Specifically, for a two-piece connector, first member 35 is connected to second member 90 by preferably threading first band fitting 50 into second band fitting 110. Subsequently, the smooth shanked portion 19 of pedicle screw 15, as depicted in FIG. 6, is inserted through first rod position 80 of first rod band 45, as depicted in FIG. 2. If connector 10 is used (as opposed to end connector 10'), a rod 20 is then inserted through second rod position 125 of second rod band 105. After inserting the rod and shanked portion 19 of pedicle screws 15 into the connectors, tightening screw 85 is then threaded through openings 65a, 65b of joining sections 60a, 60b. Tightening screw 85 is advanced within openings 65a, 65b, whereby the rod 20 and connectors 10 and/or 10' are then interlocked together by urging joining sections 60a and 60b toward each other. Note that other means of bringing together joining sections 60a and 60b are also contemplated, such as by the surgeon using a separate tool, such as pliers, followed by the placement of a permanent clip (not shown) that holds the joining sections together in their desired location. Regardless of the means used for bringing together the joining sections 60a and 60b, the movement of urging joining section 60a toward joining section 60b reduces the diameter of interior substantially conical surface 70. This reduction in diameter progressively forces exterior substantially conical surface 115 to move away from interior substantially conical surface 70. That is, the reduction in diameter of the interior substantially conical surface 70 tends to longitudinally drive exterior surface member 90' from a first position to a second position relative to first member 35. Since first rod band 45 is joined to second rod band 105 at first band fitting 50 and second band fitting 110, tension is created in first rod band 45 and second rod band 105, thereby tightening first rod band 45 around the pedicle screw 15 held within first rod position 80, and also tightening second rod band 105 around the rod 20 held within second rod position 125. The tension created in first rod band 45 and second rod band 105 creates a compression force around the shaft of pedicle screw 15 and the circumference of rod 20. Continued advancement of tightening screw 85 is performed until a sufficient tension is developed in first rod band 45 and second rod band 105 to securely hold and lock in place connector 10 with the screw 15 held in first rod position 80 and rod 20 held in the second rod position 125. This procedure is repeated for attaching a different connector to the other end of rod 20.

Figure 14:
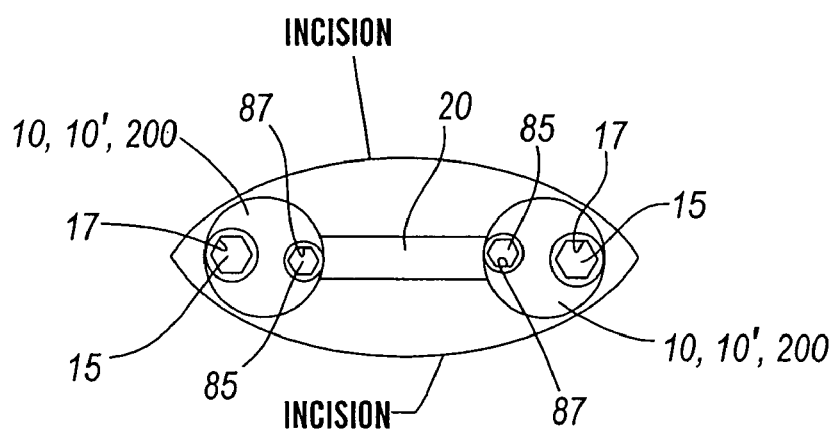
FIG. 14 is a plan view of an incision showing implantation of two connectors and a rod.

Now referring to FIG. 14, an incision is shown with the connector 10, 10' or 200 (as discussed below) used at either end of rod 20. As can be seen, both the top of the pedicle screw 15 and the top of the tightening screw 85 are accessible from the top of the incision. Therefore, using the present invention, a surgeon can make an incision that is only slightly longer than the rod to be implanted. This provides access to the surgical site for installation of the pedicle screws 15, connectors 10, 10', or 200 and the rod 20. Given that both the top of the pedicle screw 15, and the top of the tightening screws 85 are accessible, the surgeon can perform the installation of the screws 15, rod 20, and connectors 10, 10' or 200 in a minimally invasive manner. That is, excessive retraction of the incision is not necessary to gain access to the surgical site to place the implant. Furthermore, excessive retraction of tissue is also not necessary to attach, connect, and tighten the various components. In a separate aspect of the invention, pedicle screws 15 may be equipped with leaders (not shown), preferably flexible leaders, that allow the connectors 10, 10', or 200 and the rod 20 to be assembled above the top of the incision, and then slipped over the flexible leaders onto the smooth shanked portion 19 of pedicle screws 15, at which point the tightening screws 85 may be adjusted to secure the connectors 10,10', or 200, to the pedicle screws 15 and rod 20. Thereafter, the flexible leaders may be removed and the incision closed. Thus, the present invention offers a minimally invasive method for performing spinal stabilization surgery.

Figure 15:
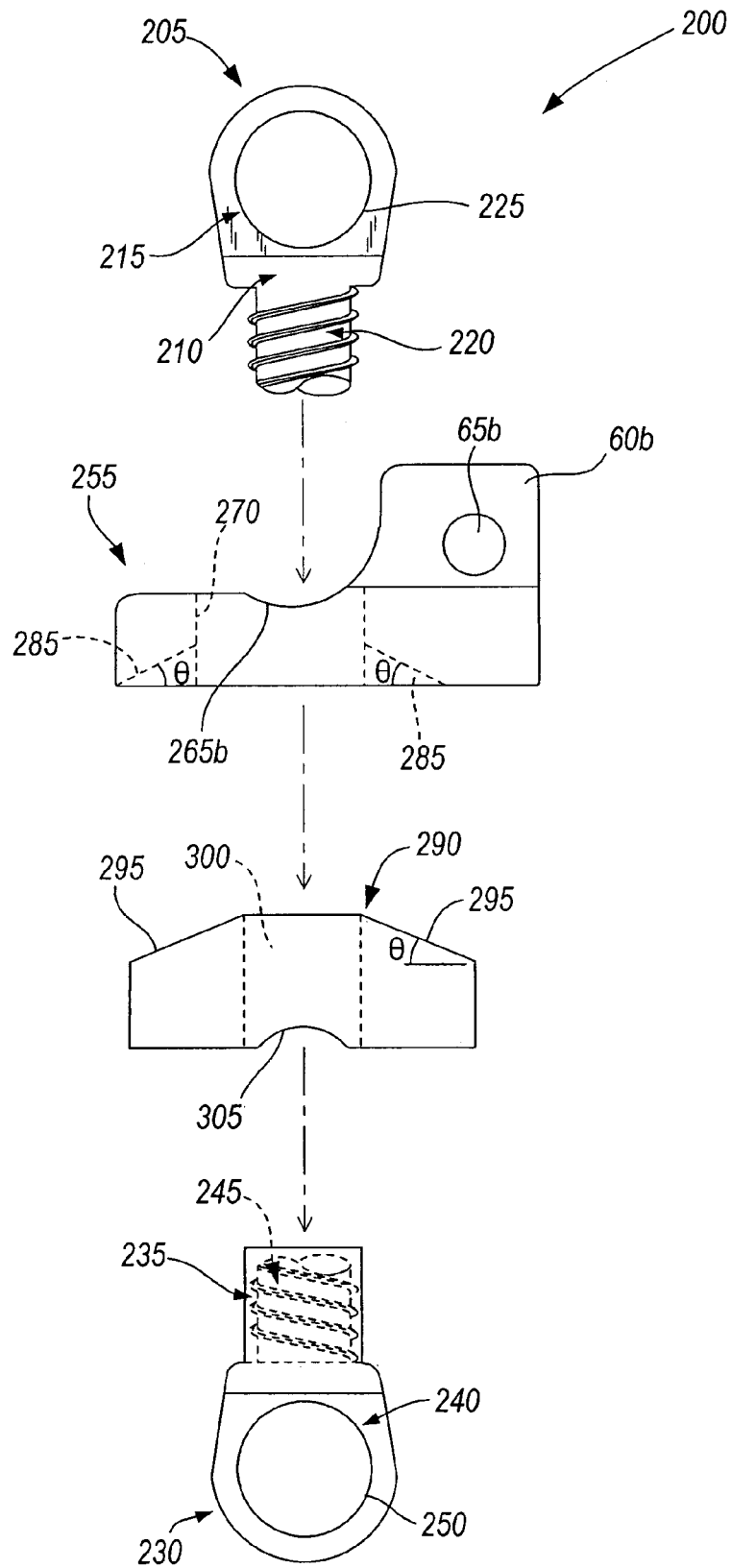
FIG. 15 is an elevation view of an exploded four-piece connector of the present invention.

In a separate embodiment, the connector is formed using more than two pieces. More particularly, the connector may be formed of three pieces, or alternately, of four pieces. Referring now to FIGS. 15-17B, connector 200, comprising four pieces, is presented. FIG. 15 shows an exploded view of a four-piece connector having conical surfaces. Connector 200 is comprised of two rod receiving members and two conical surface members. First rod receiving member 205 is shown at the top of FIG. 15. First rod receiving member 205 includes means for interconnecting first rod receiving member 205 to a second rod receiving member 230. Preferably, the means for connecting these two components comprises threads, although a hook or socket-type of interlocking means is also within the scope of the invention, as is any means for connecting the two members together. Using threaded connections to connect first rod receiving member 205 to second rod receiving member 230 provides rotational adjustability to connector 200 to accommodate the position of the two rods, such as pedicle screw 15 and rod 20. Adjustability is attained by partially releasing the tightened threads. As shown in FIG. 15, first rod receiving member 205 includes first interlocking portion 210 and first rod receiving portion 215. First interlocking portion 210 is preferably circular in cross section, and includes male threads 220. First rod receiving portion 215 is preferably rectangular or square in cross section, and includes first rod opening 225. First rod opening 225 is sized to receive a rod 20 or the smooth shaft 19 of a pedicle screw 15.

Still referring to FIG. 15, second rod receiving member 230 is shown at the bottom of the figure. Second rod receiving member 230 includes a second interlocking portion 235 and a second rod receiving portion 240. Second interlocking portion 235 is preferably circular in cross section, and includes female threads 245 that interlock with male threads 220 of first rod receiving member 205. Second rod receiving portion 240 is preferably rectangular or square in cross section, and includes second rod opening 250. Second rod opening 250 is sized to receive a rod 20 or the smooth shaft 19 of a pedicle screw 15. First rod opening 225 and second rod opening 250 are depicted in the figures to be circular; however, within this embodiment, rods of alternate shapes may be used, such as multiple-sided rods (not shown), or semicircular shafts that also have one flat side (also not shown).

The third and fourth components of connector 200 include two conical surface members. Referring now to FIGS. 15-17B, first conical surface member 255 is depicted in top and side elevation views, respectively. First conical surface member 255 includes a first central opening 260, opposing joining sections 60a, 60b, slit 55, and grooves 265a, 265b. First central opening 260 receivingly accepts first rod receiving member 205. More particularly, first central opening 260 includes a first circular opening 270 that passes through first conical surface member 255 at a position interior to slit 55. In addition, a recessed rectangular or square shaped recess 275 with flange 280 is cutout within the central area of first conical surface member 255. As such, first interlocking portion 210 of first rod receiving member 205 passes through first circular opening 270 when connector 200 is assembled. However, flange 280 of recess 275 prevents first rod receiving portion 215 of first rod receiving member 205 from passing through first central opening 260. Rather, flange 280 of recess 275 retains first rod receiving portion 215 of first rod receiving member 205. In addition, optional grooves 265a, 265b serve to cradle rod 20 when it is inserted into first rod opening 225 of first rod receiving member 205. Preferably, joining sections 60a and 60b include openings 65a and 65b, respectively, that receivingly accept a tightening screw 85. First conical surface member 255 also includes an interior substantially conical surface 285 located on the underside of first conical surface member 255, or situated on the surface of first conical surface member 255 opposite the location of grooves 265a, 265b. Interior substantially conical surface 285 of first conical surface member 255 contacts the second conical surface member 290, as described below.

Still referring to FIGS. 15-17B, second conical surface member 290 includes exterior conical surface 295, second central opening 300, and grooves 305a, 305b. Second central opening 300 includes a second circular opening 310 that passes through second conical surface member 290. A recessed rectangular or square shaped recess 315 with flange 320 is cutout within the central area of second conical surface member 290. As such, second interlocking portion 235 of second rod receiving member 230 passes through second circular opening 310 of second central opening 300 when connector 200 is assembled. However, flange 320 of recess 315 prevents second rod receiving portion 240 of second rod receiving member 230 from passing through second central opening 300. Rather, flange 320 of recess 315 retains second rod receiving portion 240 of second rod receiving member 230. In addition, optional grooves 305a, 305b serve to cradle rod 20 when it is inserted into second rod opening 250 of second rod receiving member 230.

Connector 200 is assembled by passing first rod receiving member 205 through first conical surface member 255, and by passing second rod receiving member 230 through second conical surface member 290, and subsequently interconnecting male threads 220 of first rod receiving member 205 with female threads 245 of second rod receiving member 230. First conical surface member 255 is aligned with second conical surface member 290 such that interior substantially conical surface 285 of first conical surface member 255 contacts exterior substantially conical surface 295 of second conical surface member 290. Following assembly of connector 200, a rod 20 or pedicle screw 15 is passed through first rod opening 225 of first rod receiving member 205, and through second rod opening 250 of second rod receiving member 230. Tightening screw 85 is then placed within openings 65a, 65b of joining sections 60a, 60b and is tightened. As with connector 10 of a previously discussed embodiment, the action of advancing tightening screw 85 forces together joining section 60a with joining section 60b of first conical surface member 255. The movement of advancing joining section 60a toward joining section 60b reduces the diameter of interior substantially conical surface 285. This reduction in diameter progressively forces exterior substantially conical surface 295, and therefore, second conical surface member 290, to shift relative to interior substantially conical surface 285 of first conical surface member 255. Force is then applied to rods 20 or pedicle screw 15 by grooves 265a, 265b and 305a, 305b of first conical surface member 255 and second conical surface member 290, respectively. Tightening screw 85 is advanced as necessary to develop sufficient force on rod 20 or pedicle screw 15 to secure and interlock the rod 20 or pedicle screw 15 in a desired final position.

Referring now to FIGS. 16 and 17A, in a separate aspect of the invention, surface texturing 130 may be added to a portion of optional grooves 265a and/or 265b. Similarly, as shown in FIG. 8a, surface texturing 130 may be added to a portion of optional grooves 305a and/or 305b. Preferably, surface texturing may take the form of ridges and grooves, with the ridges and valleys of the grooves preferably aligned perpendicular to the longitudinal axis of grooves 265a, 265b or 305a, 305b. The ridges and grooves of texturing 130 are preferably positioned to provide a mating surface with the exterior surface of a rod 20 or screw 15, which may also have texturing 130, and which is placed in contact with grooves 265a, 265b and/or 305a, 305b. Surface texturing 130, therefore, would tend to aid in preventing longitudinal motion of a rod 20 or screw 15 after connector 200 is tightened using tightening screw 85. Surface texturing 130, however, is considered optional, and is not necessary for the proper functioning of connector 200.

Figure 18A:
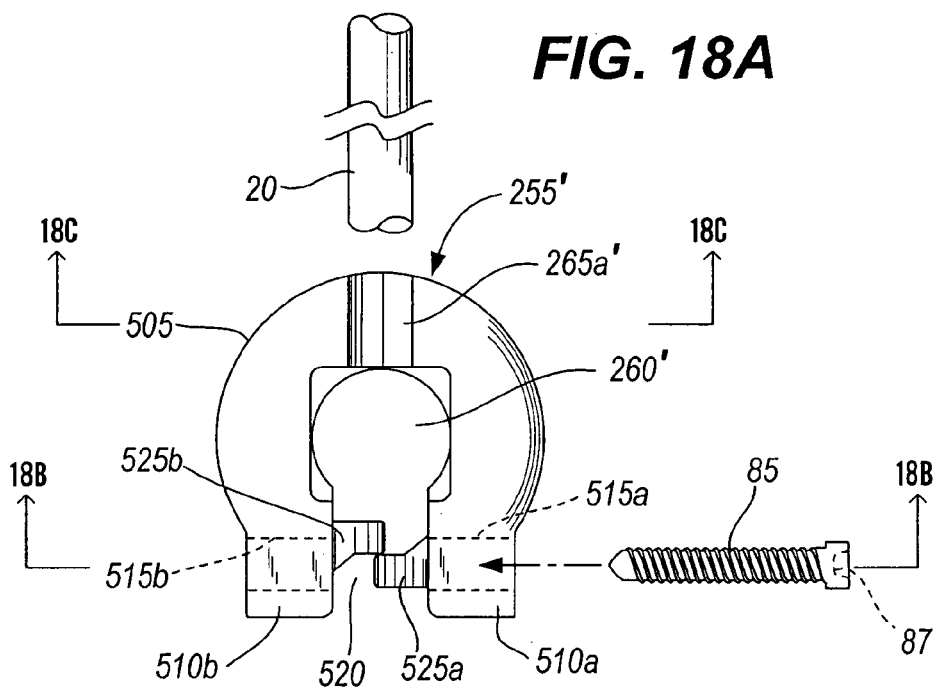
FIG. 18A is a top view component of a separate embodiment of a multi-piece connector.
Figure 18B:
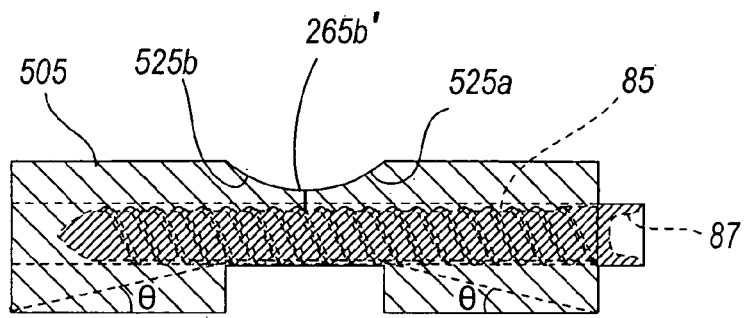
FIG. 18B is a cross-section along line 18B-18B as shown in FIG. 18A.
Figure 18C:
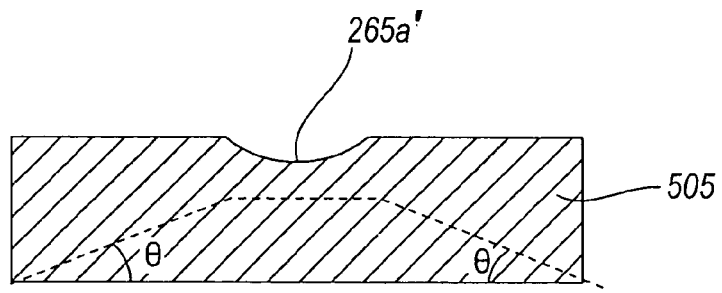
FIG. 18C is second cross-section along line 18C-18C as shown in FIG. 18A.

Referring now to FIGS. 18A-18C, in still a separate embodiment, a connector may be configured such that tightening screw 85 is aligned perpendicular to ipsilateral rod 20. More particularly, FIG. 18A depicts a top view of first conical surface member 255'. However, unlike first conical surface member 255 of connector 200, first conical surface member 255' is configured such that the longitudinal axis of tightening screw 85 is perpendicular to rod 20. First conical surface member 255' includes a first body 505, a first central opening 260', body joining sections 510a, 510b, section openings 515a, 515b, slit 520, and grooves 265a' and 265b'. First central opening 260' receivingly accepts first rod receiving member 205, in a manner similar to that previously described for connector 200. Tightening screw 85 is inserted into section openings 515a and 515b. Upon advancing tightening screw 85, body joining section 510a is drawn toward body section 510b. The interaction of the conical surfaces tighten and secure the connector in a manner similar to that described above. In addition, groove 265b' is formed by cradle wings 525a and 525b when body joining sections 510a and 510b are drawn toward each other. Thus, it can be appreciated that various configurations and orientations are possible for the tightening screw 85 relative to the rod(s) 20 and/or pedicle screw 15.

In yet a separate embodiment, a connector is formed using three portions. As described in detail above, a two piece connector, connector 10, may be formed using a first member 35 operatively associated with a second member 90. Alternately, a four piece connector, connector 200, is formed using two rod receiving members 205 and 230, and two conical surface members 255 and 290. A three piece connector is formed by combining portions of connector 10 with portions of connector 200. In one separate aspect of this embodiment, a connector is formed by combining first member 35 in combination with second rod receiving member 230 and second conical surface member 290. Alternately, in a second and separate aspect of this embodiment, a connector is formed by combining first rod receiving member 205 with first conical surface member 255, in combination with second member 90. Unitary connectors, two-piece connectors, three-piece connectors, and four-piece or more connectors allow a surgeon to customize the assembly to suit the particular patient's needs. As with connectors 10 and 200 described above, three-piece connectors are secured to the smooth shaft 19 of the pedicle crew 15 and the rod 20 by utilizing a tightening screw 85 to draw joining sections 60a and 60b together, thereby creating tension in the three-piece connector when the conical surfaces are forcibly adjusted relative to each other, wherein the tension thus created serves to grasp and secure the pedicle screw 15 and rod 20 together via the connector.

The various embodiments of the present invention use substantially conical surfaces within the connector devices. The conical surfaces may include coatings to alter the frictional characteristics of the conical surfaces. In addition, the conical surfaces may include structural modifications such as projections to reduce friction. For example, one or both of the conical surfaces may include elongated projections that run from the center of the conical surfaces to the edge of the conical surfaces. Such features would reduce the surface area that is in contact between the two conical surfaces and thereby reduce the friction created when advancing the tightening screw or the means for bringing the opposing joining sections closer to one another. Accordingly, the conical surfaces are operatively associated with each other, but are not necessarily fully in contact with each other. Indeed, a conical surface can essentially be formed by a discontinuous ridge pattern, taking the analogous form of the ribs of an umbrella or an inverted umbrella, with or without a recessed surface between the ribs. In various embodiments, spherical surfaces or spherical-like surfaces may be used within the connector. For example, the conical surfaces noted herein may be substituted with surfaces similar to that of a ball. Alternately, the conical surfaces noted herein may be substituted with undulating surfaces similar to that of a golf ball, with the individual dimpled surfaces projected outward, inward, or both.

In yet a separate aspect of the invention, the connector 10, 10' or 200 may be placed or integrally formed at the end of a rod as previously discussed, and a separate but similar connector may be placed at the other end of a different rod, with the two rods joined together in the middle by telescoping means. The telescoping means may take the form of a outer and an inner sleeve with or without a locking pin, or the telescoping means make take the form of a clamp-type of device that utilizes an outer structure to clamp around an inner rod member. This aspect of the invention allows the length of the rod to be customized at the surgical site by the surgeon.

In a separate aspect of the invention, pedicle screws 15 may be equipped with the same size head opening 17 as the head opening 87 of tightening screw 85. More particularly, as previously discussed, in a preferred embodiment, headless pedicle screws are used, such as those associated with the TSRH-3d™ spinal instrumentation manufactured by Sofamor Danek. These headless screws utilize a multi-faceted opening 17 in the head of the screw 15 to receive the tip of a tool to drive the screw 15 into the bone. The head opening 87 of tightening screw 85 can be sized to exactly match the head opening 17 of the pedicle screw 15. This offers the surgeon the ability to utilize the same tool to install pedicle screw 15 and tighten tightening screw 85.

In yet a further aspect of the invention, the head opening 17 of pedicle screw 15 may be color coded (not shown) to indicate that it is a pedicle screw 15 as opposed to the tightening screw 85. For example, head opening 17 of pedicle screw 15 may be the color white, while the head opening 87 of tightening screw 85 may be the color green. Obviously, any variation of colors could be used.

In yet a separate aspect of the present invention, different size openings may preferably be used in the head opening 17 of pedicle screw 15 and the head opening 87 of tightening screw 85. More particularly, the use of different size or shaped openings in head openings 17 of pedicle screws 15 as compared to head openings 87 in tightening screws 85 may aid in preventing confusion during surgery. That is, head openings 87 of tightening screws 85 that require a different tool to tighten than the pedicle screw 15 may assist the surgeon in not over-tightening one screw when he or she believes they are tightening the other.

Further structural aids or devices may also be employed to assist with installation of the various aspects of the present invention. For example, a torque wrench (not shown) may be used to provide the proper torque to tightening screw 85 to ensure it is not over-tightened during installation. Alternately, the head opening 87 of tightening screw 85, or head opening 17 of pedicle screw 15 may be designed to slip or create an audible clicking noise once a specified torque is reached, thereby preventing over-tightening.

The present invention has the distinct advantage of offering a very low profile device for securing two rods together, or one rod and one screw, such as a stabilizing rod and the shank of a pedicle screw. Given that the present invention offers the advantage of being very low profile, a surgeon is able to implant a stabilizing device for the spine with minimal disruption to neighboring tissue. As a result, the patient undergoes less pain, and less recovery time, and medical costs are consequently also reduced.

The structures of the present invention are made from one or more materials that possesses the appropriate strength characteristics necessary to withstand loading from the human body when used in medical applications. Preferably, materials include ceramics, plastics, metals, or carbon fiber composites. More preferably, the materials are made from titanium or stainless steel.

Devices disclosed herein can also be made of thermal memory materials or materials that possess different elastic properties at varying temperatures. In this aspect of the invention, the subject component(s) may be heated or cooled to a desired temperature, implanted, then subsequently allowed to cool or warm to the temperature of the ambient conditions that will exist during the usage period for the subject device, namely, normal body temperature.

It is to be understood that the present invention has application to medical devices other than spinal implants. For example, the present invention can be used in external fixator systems. Specifically, connectors are used to secure rods to screws that project outside of the skin surface. The present invention offers a low-profile system of connecting two rods, or a rod to the shaft of a screw. In addition, the present invention may be used to secure various orthodontic appliances. For example, it maybe used to secure arch wires to brackets. Alternately, it may be used in various orthodontic headgear apparatus.

Furthermore, it is understood that the present invention has application outside the medical field. The securing mechanism of the present invention is not limited to medical implants. The present invention could be used to secure any two wires, screws, rods, or a combination of these such devices, such as in linking mechanisms, and has application to any type of mechanical device with static or moving parts. Other applications, by no means exhaustive, may include connecting legs of a tripod to a base and mounting track lighting fixtures. One of skill in various of the construction arts will appreciate how to make and use the present invention in view of the guidance provided herein (with respect to a surgical application) and in view of the Figures set forth herein.

While various embodiments of the present invention have been described in detail, it is apparent that modifications and adaptations of those embodiments will occur to those skilled in the art. However, it is to be expressly understood that such modifications and adaptations are within the spirit and scope of the present invention, as set forth in the following claims.

What is claimed is:

1. A connector for securing together two rods, comprising:
   (a) a body including:
      a first substantially truncated conical surface having a slit comprising an open arc in the first substantially truncated conical surface, the slit passing through said first substantially truncated conical surface, and opposing joining sections adjacent said slit;
      a first receptacle comprising a rod band for receiving a first of said two rods, the first rod band comprising a first rod band fitting;
      a second receptacle for receiving a second of said two rods;
      a second substantially truncated conical surface in at least partial contact with said first substantially truncated conical surface; and
   (b) a means for urging said opposing joining sections toward each other;
   wherein a diameter of said first substantially truncated conical surface decreases upon operating the means for urging said opposing joining sections toward each other causing said first substantially truncated conical surface to act against said second substantially truncated conical surface to tighten the first and second receptacles, and wherein said two rods are interlocked by said connector upon urging said opposing joining sections toward each other.

2. The connector as claimed in claim 1, wherein said body is of two-piece construction.

3. The connector as claimed in claim 1, wherein said means for forcing comprises a tightening screw.

4. The connector as claimed in claim 1,
   wherein said first substantially truncated conical surface has an angle of between about 20 and 60 degrees.

5. The connector as claimed in claim 1, wherein said first substantially truncated conical surface has an angle of between about 30 and 45 degrees.

6. The connector as claimed in claim 1, wherein said second receptacle comprises a rod band.

7. The connector as claimed in claim 6, wherein said rod band comprises a second rod band fitting.

8. The connector as claimed in claim 1, wherein said first receptacle is adapted for receiving a shank of a pedicle screw.

9. The connector as claimed in claim 1, wherein said second receptacle is adapted for receiving a spinal stabilizing rod.

10. The connector as claimed in claim 1, wherein said first receptacle is threaded to said second receptacle.

11. The connector as claimed in claim 1, wherein said first receptacle further comprises surface texturing.

12. The connector as claimed in claim 1, wherein said second receptacle further comprises surface texturing.

13. A connector for securing two rods, comprising:
   (a) a first member including a first receptacle for receiving a first of said two rods, a first substantially truncated conical surface having a slit, the slit passing through said first substantially truncated conical surface, and opposing joining sections adjacent said slit;
   (b) a second member including a second receptacle for receiving a second of said two rods, a second substantially truncated conical surface at least partially contacting said first substantially truncated conical surface, said second member connected to said first member;
   (c) means for urging said opposing joining sections together;
   wherein a diameter of said first substantially truncated conical surface decreases upon operating the means for urging said opposing joining sections toward each other, and wherein upon forcing said opposing joining sections in closer proximity said second substantially conical surface is forced to move, causing a tension force to be created within said first member and said second member securing said two rods to the connector.

14. The connector as claimed in claim 13, wherein said means for urging comprises a tightening screw.

15. The connector as claimed in claim 13, wherein said first substantially truncated conical surface has an angle of between about 30 and 45 degrees.

16. The connector as claimed in claim 13, wherein said first receptacle comprises a band.

17. The connector as claimed in claim 13, wherein said second receptacle comprises a band.

18. The connector as claimed in claim 13, wherein said first receptacle is adapted for receiving a shank of a pedicle screw.

19. The connector as claimed in claim 13, wherein said second receptacle is adapted for receiving a spinal stabilizing rod.

20. The connector as claimed in claim 13, wherein said first member is threaded to said second member.

21. A connector for securing a rod and a shaft of a pedicle screw, comprising:
   (a) a first member including an interior substantially truncated conical surface having a first central opening and a slit with adjacent opposing joining sections, said first member further including a first rod band with a portion of said first rod band at least partially disposed through said first central opening;
   (b) a second member including an exterior substantially truncated conical surface formed for contacting said interior substantially truncated conical surface, said second member including a second central opening and a second rod band at least partially disposed through said second central opening;
   (c) means for interconnecting said first rod band to said second rod band; and
   (d) means for forcing said opposing joining sections toward each other;
   wherein a diameter of said interior substantially truncated conical surface decreases upon operating the means for forcing said opposing joining sections toward each other, and wherein the rod is placed through either said first rod band or said second rod band, and the shaft of the pedicle screw is placed through the remaining of either of said first rod band or said second rod band.

22. The connector as claimed in claim 21, wherein said means for interconnecting comprises a threaded connection.

23. The connector as claimed in claim 21, wherein said means for interconnecting comprises a welded connection.

24. The connector as claimed in claim 21, wherein said means for forcing comprises a threaded screw.

25. The connector as claimed in claim 21, wherein said interior substantially truncated conical surface has an angle of between about 20 and 60 degrees.

26. A method of securing a pedicle screw that has been implanted in a patient to a stabilizing rod, said method comprising:
   (a) inserting an exposed shaft of the pedicle screw and the stabilizing rod into a connector, the connector comprising separate receptacles for receiving the pedicle screw shaft and the stabilizing rod, the connector further including a first substantially truncated conical surface having a slit and opposing joining sections adjacent to the slit, the connector including a second substantially truncated conical surface at least partially contacting the first substantially truncated conical surface;
   (b) inserting a tightening screw into openings in the opposing joining sections; and
   (c) tightening the tightening screw to force the opposing joining sections toward each other;
   wherein said tightening step decreases a diameter of the first substantially truncated conical surface which pushes against the second substantially truncated conical surface which causes the second substantially truncated conical surface to move, which places a constricting force around the pedicle screw shaft and the stabilizing rod through the receptacles.

27. The method as claimed in claim 26, further comprising the step of rotating said connector.

28. A connector device for attachment to a spinal implant including a rod, comprising:
   a first truncated conical surface having a slit separating opposing joining sections of said first truncated conical surface;
   a second truncated conical surface for contacting at least a portion of said first truncated conical surface, said second truncated conical surface in operative association with said first truncated conical surface;
   at least one band connected to at least one of said first or second truncated conical surfaces, said band for receiving at least a portion of the rod; and
   a means for at least partially closing the opposing joining sections toward each other;
   wherein a diameter of said first truncated conical surface decreases upon operating the means for at least partially closing, wherein said first truncated conical surface acts against said second truncated conical surface causing the first substantially truncated conical surface to move, causing the band to tighten around said portion of the rod to secure the connector device to the rod.

29. The connector device as claimed in claim 28, wherein said first truncated conical surface, said second truncated conical surface and said band comprise a plurality of members.

30. The connector device as claimed in claim 28, further comprising a second band for receiving a second rod, said second band connected to at least one of said first or second truncated conical surfaces, wherein said second band secures said second rod upon operating the means for at least partially closing.

31. The connector device as claimed in claim 28, wherein one of said first or second truncated conical surfaces includes a rod integrally connected thereto.

32. The connector device as claimed in claim 28, wherein the rod comprises a shaft of a pedicle screw.

33. A connector device for attachment to a spinal implant including a rod, comprising:
   a plurality of truncated conical surfaces, at least one of said plurality of truncated conical surfaces comprising a means for decreasing a diameter of said at least one of said plurality of truncated conical surfaces by at least partially closing an open arc in at least one of said plurality of truncated conical surfaces causing a second truncated conical surface to move;
   a means for engaging at least a portion of the rod, wherein the means for engaging is operatively associated with said plurality of truncated conical surfaces;
   wherein said plurality of truncated conical surfaces comprises a first truncated conical surface in at least partial contact with a second truncated conical surface;
   wherein the means for engaging secures the rod to said at least one of said plurality of truncated conical surfaces upon operation of said means for decreasing.

34. The connector device as claimed in claim 33, wherein said plurality of truncated conical surfaces and said means for engaging comprise a plurality of members.

35. The connector device as claimed in claim 33, further comprising a second means for engaging one of a pedicle screw or a second rod, said second means for engaging operatively associated with said plurality of truncated conical surfaces, wherein the second means for engaging secures the second rod or the pedicle screw to said plurality of truncated conical surfaces upon operation of said means for decreasing.

36. The connector device as claimed in claim 33, wherein one of said plurality of truncated conical surfaces includes a rod integrally connected thereto.

37. The connector device as claimed in claim 33, wherein the rod comprises a shaft of a pedicle screw.

* * * * *